(12) United States Patent
Voellmy

(10) Patent No.: US 7,053,052 B2
(45) Date of Patent: May 30, 2006

(54) THERAPIES INVOLVING MUTATED HEAT SHOCK TRANSCRIPTION FACTOR

(76) Inventor: Richard W. Voellmy, 7240 SW. 124 South St., Miami, FL (US) 33136

( * ) Notice: Subject to any disclaimer, the term of this patent is extended or adjusted under 35 U.S.C. 154(b) by 15 days.

(21) Appl. No.: 10/984,917

(22) Filed: Nov. 10, 2004

(65) Prior Publication Data

US 2005/0192219 A1    Sep. 1, 2005

Related U.S. Application Data

(60) Division of application No. 09/547,808, filed on Apr. 11, 2000, which is a continuation of application No. 09/010,163, filed on Jan. 21, 1998, now abandoned, which is a continuation-in-part of application No. 08/914,646, filed on Aug. 19, 1997, now abandoned.

(60) Provisional application No. 60/035,662, filed on Jan. 21, 1997.

(51) Int. Cl.
*A61K 38/17*     (2006.01)
*A61K 31/7088*   (2006.01)

(52) U.S. Cl. .......................................... 514/12; 514/44
(58) Field of Classification Search .................... None
See application file for complete search history.

(56) References Cited

OTHER PUBLICATIONS

Zuo et al, Molecular and Cellular Biology, Aug. 1995, vol. 15, No. 8, pp. 4319-4330.*

* cited by examiner

*Primary Examiner*—Terry McKelvey
(74) *Attorney, Agent, or Firm*—Richard Voellmy

(57) ABSTRACT

The present invention relates to exogenous mutant HSF (mutHSF encoded by exogenous DNA) alters expression or synthesis of endogenous heat shock protein (hsp) genes in eukaryotic cells, tissues and organisms (e.g., mammalian, particularly human, cells, tissues and organisms). As described herein, mutHSF has been shown to regulate expression of endogenous hsp in cells and, as a result, to alter the response of the cells to stress. The mutHSF of the present invention is either positively-acting mutHSF or negatively-acting mutHSF.

7 Claims, 4 Drawing Sheets

FIGURE 1

THERAPIES INVOLVING MUTATED HEAT SHOCK TRANSCRIPTION FACTOR

RELATED APPLICATION(S)

This application is a divisional application of application Ser. No. 09/547,808, filed Apr. 11, 2000, which is a continuation of application Ser. No. 09/010,163 (ABN), filed Jan. 21, 1998, which is a Continuation-in-Part of application Ser. No. 08/914,646 (ABN), filed Aug. 19, 1997, which claims the benefit of U.S. Provisional No. 60/035,662, filed Jan. 21, 1997, entitled "Therapies Involving Mutated Heat Shock Transcription Factor HSF", by Richard W. Voellmy. The teachings of U.S. application Ser. Nos. 08/914,646 and 60/035,662 are incorporated herein by reference in their entirety.

GOVERNMENT SUPPORT

This invention was made in part with support under a National Institutes of Health grant (GM 32115). The U.S. Government has certain rights in the invention.

BACKGROUND OF THE INVENTION

Pre-exposure of cells, tissues or organisms to a sublethal heat shock renders them resistant to subsequent exposure to severe heat treatments that are normally lethal (Parsell, D. A., and Lindquist, S., *Annu. Rev. Genet.*, 27:437–496 (1993)). This phenomenon is known as thermotolerance. The preexposure also causes enhanced expression of a group of proteins referred to as heat shock proteins (hsp).

Pre-exposure to heat renders cells tolerant not only to subsequent exposure to severe heat, but also to certain other stresses, including ischemic type damage. This has been shown not only in experiments involving cultured cells, but also in intact organs such as, for example, the heart (Richard, V., R. et al., *Fund. Clin. Pharmacol.*, 10:409–415 (1996)).

SUMMARY OF THE INVENTION

As described herein, exogenous mutant heat shock transcription factor (mutHSF encoded by exogenous DNA) alters expression or synthesis of endogenous heat shock protein (hsp) genes in eukaryotic cells, tissues and organisms (e.g., mammalian, particularly human, cells, tissues and organisms). As also described herein, mutHSF has been shown to regulate expression of endogenous hsp in cells and, as a result, to alter the response of the cells to stress. The mutHSF of the present invention is either positively-acting mutHSF (also referred to herein as HSF1(+)) or negatively-acting mutHSF (also referred to herein as (HSF1(−)).

In one embodiment, the invention relates to a method of enhancing synthesis of hsp in a cell (e.g., an isolated cell, tissue, organ; or in cells, tissues or organs of an individual) wherein a positively-acting mutHSF or DNA encoding positively-acting mutHSF in an expressible form is introduced into the cell in a quantity sufficient and under conditions appropriate for the mutHSF to enhance hsp synthesis. In another embodiment, the present invention relates to a method of enhancing synthesis of hsp in an individual comprising administering to the individual positively-acting HSF in a quantity sufficient and under conditions appropriate for the mutHSF to be introduced into cells of the individual and enhance hsp synthesis. As used herein the term "positively-acting mutHSF" refers to mutHSF which upregulates or enhances synthesis of endogenous hsp when introduced into cells. As also used herein, the term "enhanced expression of" or "upregulated expression of" endogenous hsp refers to increased expression of endogenous hsp as a result of stress or a positively-acting mutHSF. Enhanced, induced or upregulated expression (overexpression) of endogenous hsp refers to expression or synthesis of hsp which is greater than that which occurs in the absence of stress or a positively-acting mutHSF. Expression of endogenous hsp can be enhanced or increased in cells as a result of the actions of positively-acting mutHSF, with the result that the cells are in a protected state, i.e., are protected, wholly or partially, against stress or other adverse conditions (e.g., toxic agents, UVB exposure, ischemia/reperfusion including inflammatory reactions associated with this type of injury, sepsis, acute respiratory disease, chemotherapeutic agents or other drugs) to which they are subjected. Positively-acting mutHSF can also be used to upregulate hsp expression in cells, with the result that the cells (e.g., cancer cells) are targeted for immune recognition and eliminated.

The present invention also relates to a method of inducing a protected state in a cell wherein a positively-acting mutHSF or DNA encoding mutHSF in expressible form is introduced the cell in a quantity sufficient and under conditions appropriate for the mutHSF to activate hsp synthesis. In another embodiment, the invention relates to a method of inducing a protected state in the cells of an individual in need thereof (e.g., to protect the individual's cells from chemotherapy, UVB, sepsis, ischemia), comprising administering to the individual a positively-acting mutHSF in a quantity sufficient and under conditions appropriate for the mutHSF to be introduced into cells of the individual and enhance hsp synthesis, thereby producing a protected state. In a particular embodiment, the present invention relates to a method of inducing an anti-inflammatory effect in a cell, tissue, or organism, comprising introducing into the cell, tissue or organism a positively-acting mutHSF or DNA encoding a positively-acting mutHSF in expressible form in a quantity sufficient and under conditions appropriate for the mutHSF to activate hsp synthesis and cause an anti-inflammatory reaction (effect) to occur.

In another embodiment, the invention relates to a method of inhibiting (completely or partially) hsp synthesis in a cell wherein a negatively-acting mutHSF or DNA encoding negatively-acting mutHSF in an expressible form is introduced into the cell in a quantity sufficient and under conditions appropriate for the mutHSF to inhibit stress-induced hsp synthesis. As used herein the term "negatively-acting mutHSF" refers to mutHSF which downregulates or inhibits stress-induced synthesis of endogenous hsp when introduced into cells. As also defined herein, inhibited, reduced or downregulated expression of stress-induced endogenous hsp refers to reduction of hsp expression or synthesis which occurs to a greater extent than that which occurs in the absence of negatively-acting mutHSF. Expression of endogenous hsp can be inhibited (completely or partially) or reduced in cells during stress or adverse conditions as a result of the actions of negatively-acting mutHSF, with the result that the cells are sensitized to heat and other kinds of stresses i.e., are in an sensitized state. For example, negatively-acting mutHSF can be used to target killing of tumor cells to killing by heat and/or other kinds of stresses.

Positively-acting mutHSF of the present invention minimally includes a heat shock element (HSE) DNA-binding domain, a HSF oligomerization domain (trimerization domain) such as, for example, all or a portion of hydrophobic repeat one from any HSF, a nuclear localization signal and a transcription activation domain. A preferred type of negatively-acting HSF minimally includes an HSE DNA-binding domain, a HSF oligomerization domain and a nuclear localization signal. Positively-acting mutHSF refers to a HSF (e.g., mammalian HSF, particularly human HSF1) molecule mutated in at least one amino acid residue within the regulatory region of a HSF. Negatively-acting HSF refers to a HSF molecule mutated in one or more of the activation domains or altered in the DNA-binding domain. In a particular embodiment, negatively-acting mutHSF is a HSF molecule in which mutations are present in two of the activation domains of HSF.

DNA encoding mutHSF is also the subject of the present invention.

In the method of altering (enhancing/upregulating or inhibiting/downregulating) expression of hsp in a cell (tissue or organism), mutHSF or nucleic acid (DNA or RNA) encoding mutHSF is introduced into the cell under conditions appropriate for mutHSF to alter expression of the hsp. In one embodiment, a vector comprising a nucleic acid encoding mutHSF in expressible form is introduced into a cell where the mutHSF is transcribed and translated from the nucleic acid sequence; the mutHSF is produced, enters the cell nucleus and binds a HSE, where the mutHSF is transcribed from the nucleic acid sequence; the mutHSF produced binds a HSE, resulting in expression of hsp encoded by the DNA which includes the HSE to which a mutHSF binds. Alternatively, mutHSF is introduced into the cell, enters the cell nucleus and binds a HSE, resulting in expression of the encoded hsp. In either approach, cells which express the mutHSF can be introduced into an individual. DNA encoding mutHSF can also be administered to an individual, such as by gene therapy methods in which the DNA is introduced into the individual in expressible form and enters cells in which mutHSF is to be expressed and upon expression of mutHSF in the cell, the mutHSF acts in the cell nuclei to enhance endogenous hsp expression. Alternatively, mutHSF itself, contained in an appropriate vehicle, is introduced into the individual and enters cells, in which it acts to enhance hsp production. In either case, mutHSF binds a HSE, resulting in expression of the encoded hsp in sufficient quantity to produce the desired effect of inducing a protected state. In one embodiment, for example, DNA encoding positively-acting mutHSF comprising a HSE DNA-binding domain; a HSF oligomerization domain, a nuclear localization signal and a transcription activation domain or mutHSF containing these elements is introduced into an individual in need of upregulation (enhancement) of hsp expression, in sufficient quantity to result in enhanced hsp expression. In one embodiment, general upregulation of all types of hsp (e.g., hsp70, hsp25, hsp60, hsc70 and hsp90) in cells occurs, resulting in protection of the cells against stress or other adverse conditions.

The mutHSF and methods described herein are useful to treat or prevent a variety of conditions or diseases. Upregulation of hsp synthesis is beneficial in applications in which, for example, protection against damage caused by hyperthermia, oxidative stress, toxicant exposure (e.g., toxic metabolites such as nitric oxide), UVB exposure, ischemia/reperfusion occurring under various different circumstances, sepsis and acute respiratory disease is desired. Upregulation is also useful to reduce inflammatory type responses (e.g., synthesis of and toxicity caused by inflammatory mediators such as inflammatory cytokines, lipopolysaccharide (LPS) and tumor necrosis factor (TNF)) and negative consequences, such as, for example, in neurologic injury caused by activation of excitatory amino acid receptors or in restenosis following angioplasty. Upregulation is also useful to render non-target cells (normal cells) resistant to chemotherapeutic agents. Upregulation of hsps in cancer cells is also expected to render them targets for immune recognition and elimination. In one embodiment, the present invention relates to a method of inducing a protected state in a cell by introducing into the cell a positively-acting mutHSF in a quantity sufficient and under conditions appropriate for the mutHSF to activate hsp synthesis. In another embodiment, the present invention relates to a method of protecting a cell (e.g., one or more cells of an individual) against ischemia damage, comprising introducing into the cell (e.g., or the cells of the individual) a positively-acting mutHSF to enhance hsp synthesis. In another embodiment the invention relates to a method for enhancing the immunogenicity of a cancer cell comprising providing the cell with a positively-acting mutHSF in a quantity sufficient for the mutHSF to enhance hsp synthesis. In yet another embodiment the invention relates to a method of increasing the immunogenicity of a tumor cell comprising administering to the individual positively-acting mutHSF in a quantity sufficient and under conditions appropriate for the mutHSF to be introduced into the tumor cells of the individual, thereby enhancing hsp synthesis in the tumor cell.

Alternatively, downregulation of hsp synthesis is useful, for example, to sensitize cells to stressful conditions, thus enhancing, for example, the potency of anti-cancer drugs, or to induce apoptotic death. In one embodiment the present invention relates to a method of increasing the sensitivity of a cell to a physical or chemical stress i.e., of inducing a sensitized state, comprising providing the cell with a negatively-acting mutHSF in a quantity sufficient to inhibit (prevent or decrease), completely or partially, hsp synthesis normally induced by the stress.

BRIEF DESCRIPTION OF THE DRAWINGS

FIG. 1 is the SEQ ID NO:1 amino acid sequence of human heat shock transcription factor (HSF1) (SEQ ID NO:2).

DETAILED DESCRIPTION OF THE INVENTION

Figure 2:
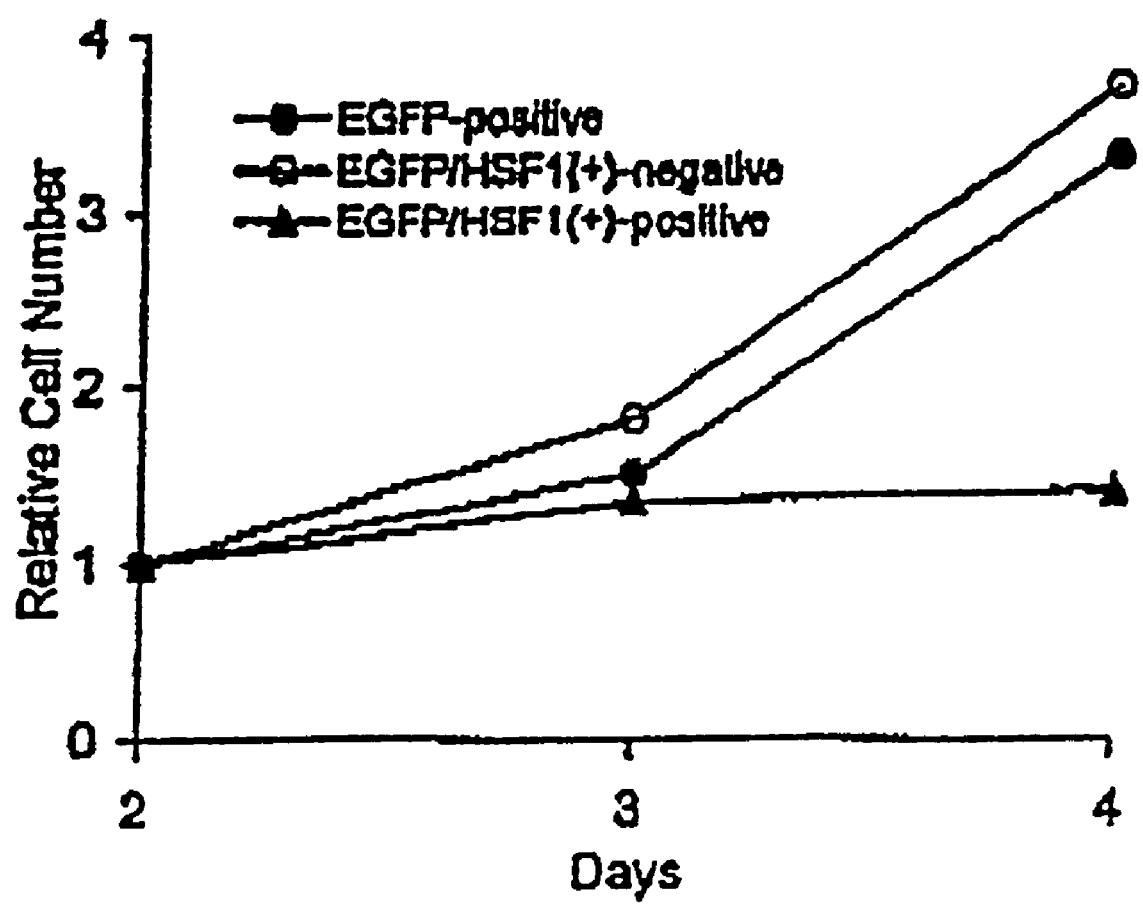
FIG. 2 is a graph of days versus relative cell number showing that elevated hsp levels severely inhibited cell proliferation.

The present invention relates to the modulation or alteration of heat shock protein (hsp) gene expression (hsp synthesis) in cells through introduction into the cells of a mutated heat shock transcription factor (mutHSF) or a gene encoding in expressible form a mutHSF, with the result that hsp synthesis in the recipient cells is modulated or altered (upregulated or downregulated).

Transcription of the stress-inducible hsp genes is regulated by the activity of heat shock transcription factor (HSF). In vertebrate cells, transcription of the stress-inducible hsp genes is regulated by the activity of heat shock transcription factor 1 (HSF1). This factor binds to the HSE sequence present in all promoters of stress-inducible hsp genes which results in enhanced synthesis of hsp mRNAs. Synthesis of hsp is well known to be further subject to posttranscriptional and translation controls. HSF is present in both unstressed and stressed cells, but only becomes an active transcription factor upon stress. Activation of the factor involves a complex series of regulatory events. Normally, i.e., in unstressed cells, HSF is monomeric, probably stabilized by intramolecular hydrophobic interactions and complexed with a repressor protein(s). In this form HSF is incapable of DNA binding. Upon stress, the repressor protein(s) is released, hydrophobic interactions are disrupted, the factor becomes homotrimeric and, as a consequence, acquires HSE DNA-binding activity and relocates to the nucleus. A further, independent conformational change, possibly induced by phosphorylation, is required to enable the trimeric factor to stimulate transcription of hsp genes.

Transfection of mammalian cells with a gene encoding human HSF1 resulted in the synthesis of HSF1 in an amount that greatly exceeded that of endogenous HSF1 (Zuo, J., et al., *Mol. Cell Biol.*, 15:4319–4330 (1995)). HSF1 expressed from the transfected gene was trimeric, HSE DNA-binding and nuclear-localized. Hence, overexpression of HSF1 bypasses some of the regulatory controls that normally keep the factor monomeric and non-DNA-binding. However, overexpressed HSF1 was incapable of stimulating transcription from a reporter gene controlled by a hsp gene promoter.

Figure 1:
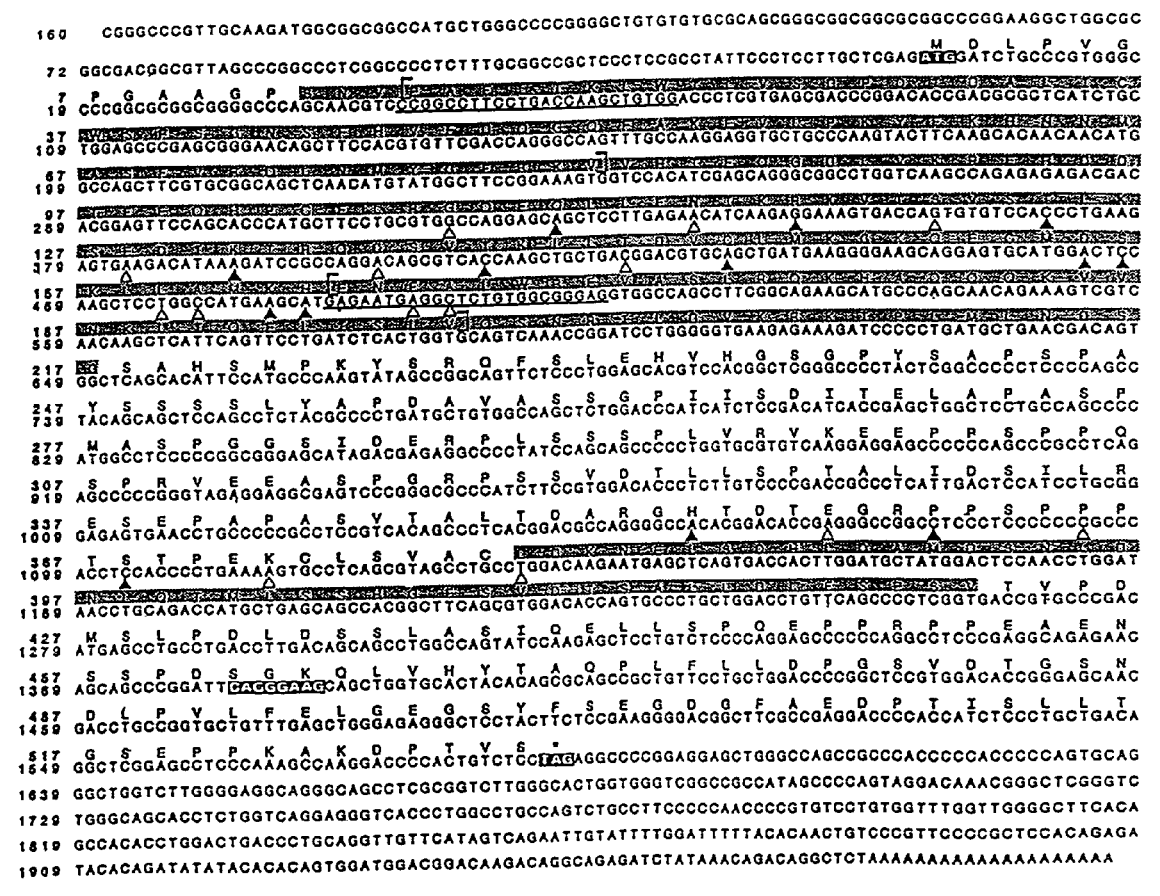

The present invention is based on the discovery that mutHSF modulates expression of endogenous hsp and, as a result, alters the susceptibility of cells to stress. As described herein, mutation of a regulatory region, spanning amino acids from about 180 to about 315 in the human HSF1 sequence (FIG. 1), results in a factor (positively-acting mutHSF) that is capable of activating hsp synthesis in the absence of stress. As also described herein, a mutHSF is capable of enhancing the expression of endogenous hsp genes, such as the genes encoding hsp90, hsc70, hsp70, hsp60 and hsp25. Also described herein is mutation of a second region, including transcription activation domains, spanning amino acids from about 277 to about 529 in the human HSF1 sequence, which results in a factor (a negatively-acting mutHSF) that is capable of inhibiting hsp synthesis induced by stress in the presence of stress.

The present invention relates to an exogenous mutHSF, which is HSF encoded by exogenous DNA and which alters expression or synthesis of endogenous hsp genes when present in eukaryotic cells, tissues or organisms (e.g., mammalian, particularly human, cells, tissues or organisms). As described herein, mutHSF has been shown to regulate expression of endogenous hsp in cells and, as a result, to alter the response of the cells to stress. The mutHSF of the present invention is either positively-acting mutHSF or negatively-acting mutHSF.

In one embodiment, the present invention relates to a method of enhancing synthesis of hsp in a cell, tissue or organism wherein a positively-acting mutHSF is introduced into the cell, tissue or organism in a quantity sufficient and under conditions appropriate for the positively-acting mutHSF to enhance hsp synthesis, with the result that the cells are protected, wholly or in part, against stress or other adverse conditions, e.g., UVB exposure, ischemia/reperfusion including inflammation reactions associated with this type of injury, sepsis, high concentration of excitatory amino acids in the case of neural cells, inflammatory mediators such as LPS and TFN, toxic metabolites such as nitric oxide and chemotherapeutic agents, to which they are subjected. In another embodiment, a positively-acting mutHSF is used to upregulate hsp expression in tumor cells, with the result that the tumor cells are targeted for immune recognition and elimination.

In another embodiment, the present invention relates to a method of inhibiting (completely or partially) synthesis of hsp in a cell wherein a negatively-acting mutHSF is introduced into the cell in a quantity sufficient and under conditions appropriate for the negatively-acting mutHSF to inhibit hsp synthesis, during stress or under adverse conditions. Negatively-acting mutHSF sensitizes cells to heat and other kinds of stress, and finds application in targeted killing of tumor cells.

MutHSF for use in the present invention can be obtained from a variety of sources. For example, mutHSF can be obtained from natural sources, recombinantly produced or chemically synthesized. HSF was initially characterized as a factor capable of binding HSEs (Voellmy, R., *Crit. Rev. Eukaryotic Gene Expr.*, 4:357–401 (1994); Voellmy, R., In: *Stress-Inducible Cellular Responses* (Feige, U. et al. eds.), Birkhauser Verlag, Basel, Switzerland, pp. 121–137 (1996)). HSEs are short, double-stranded nucleotide sequences whose minimal structure is 5' NGAANNTTCNNGAAN (SEQ ID NO.3); they are typically present in the promoters of hsp genes. Deletion studies of promoters of hsp genes revealed that HSE sequences are required for heat-induced transcription from these promoters. HSF purified from stressed cells were (Goldenberg, J., et al., *J. Biol. Chem.* 263:19734–19739 (1988)) shown to be capable of stimulating transcription from an hsp promoter in vitro.

cDNAs for HSF were cloned from a number of organisms, including yeast, plant species, *Drosophila melanogaster, Xenopus laevis,* mouse, chicken and man (Voellmy, R., *Crit. Rev. Eukaryotic Gene Expr.,* 4:357–401 (1994)). Several conserved features were discovered from sequence comparisons (Nakai, A. and Morimoto, R. I., *Mol. Cell Biol.,* 13:1983–1997 (1993)). All HSF species appear to have an HSE DNA-binding domain located near the amino terminus of the molecules. The DNA-binding domain is followed by two closely spaced hydrophobic repeats of the 3,4 type. Each of these hydrophobic repeats contains two hydrophobic faces; the term 3,4 type refers to the relationship between them. Part of this hydrophobic stretch is responsible for holding together the active trimeric factor. A third hydrophobic repeat region is located at a distance from the first two hydrophobic repeats. While the overall sequence similarity between HSFs from different organisms or between different HSFs from the same organism (see below) is low, the DNA-binding region and the hydrophobic regions are well conserved (Nakai, A. and Morimoto, R. I., *Mol. Cell Biol.,* 13:1983–1997 (1993)).

Surprisingly, vertebrates appear to contain two or more different types of HSF. Two HSF genes were cloned from human cells. The encoded factors are referred to as HSF1 and HSF2 (see Rabindran, S. K., et al., *Proc. Natl. Acad. Sci., USA* 88:6906–6910 (1991) for cloning of human HSF1). Antibodies specific to HSF1 and HSF2 were prepared and used to demonstrate by an antibody supershift experiment that a large portion of the heat-induced HSE DNA-binding activity is due to HSF1 (Baler, R. et al., *Mol. Cell Biol.,* 13:2486–2496 (1993)). Consequently, it was proposed that HSF1 is the factor responsible for the stress activation of hsp genes. The supershift experiment remains inconclusive, however, because it cannot be estimated how much transcription factor is needed to activate an hsp gene. Thus, it is conceivable that a minor DNA-binding activity overlooked in the supershift experiment is, in fact, regulating hsp genes. Prior to Applicant's discovery, proof had not been provided that HSF1 is indeed a stress regulator of endogenous, i.e., chromosomally located, hsp genes or that it can alone i.e., without any other stress-induced factor, activate these hsp genes.

To examine HSF structure/function, HSF1 mRNA was prepared in an in vitro transcription reaction using as the template a human HSF1 (hHSF1) cDNA. When this mRNA was microinjected into *Xenopus laevis* stage 6 oocytes, the oocytes synthesized hHSF1 (Baler, R., et al., *Mol. Cell Biol.*, 13:2486–2496 (1993)). Like endogenous HSF1 in unstressed cells, the hHSF1 produced, referred to as overexpressed hHSF1, was partly monomeric and partly in a 1:1 complex with hsp70, and was incapable of binding DNA. Heat treatment of the injected oocytes caused hHSF1 to homotrimerize and to acquire HSE DNA-binding ability. To determine whether hHSF1 was also induced to become transcriptionally active by the heat shock treatment, the HSE DNA-binding domain was replaced by the DNA-binding domain of bacterial repressor protein LexA. When mRNA for the LexA-hHSF1 chimera was injected into oocytes, monomeric chimeric factor was synthesized. The monomeric chimeric factor was induced by heat shock treatment to trimerize and acquired the ability to bind a LexA consensus recognition sequence. The heat-activated chimeric factor was also shown to enhance expression from a nuclear-injected chloramphenicol acetyltransferase (CAT) reporter gene controlled by a basal promoter supplemented by LexA binding sites (LexA-CAT) (Zuo, J. et al., *Mol. Cell Biol.*, 14:7557–7568 (1994); Zuo, J., et al., *Mol. Cell Biol.*, 15:4319–4330 (1995)).

Analyses of hHSF1 mutants in the oocyte microinjection system revealed the functional importance of the different hydrophobic repeats. Repeat 1 was required for factor trimerization. Repeats 2 and 3, as well as sequences at the amino-terminal end of repeat 1, were essential for maintaining the factor in a monomeric, non-DNA-binding form in the absence of heat shock (Zuo, J. et al., *Mol. Cell. Biol.*, 14:7557–7568 (1994)). Deletion of repeat 2 rendered the factor trimeric as well as transcriptionally active, whereas mutations in the other repeats only caused factor trimerization, but did not result in transcriptionally active factor. Mutations in the region following the second repeat (amino acids 203 to 315) did not cause factor trimerization, but activated the transcriptional competence of the factor caused to be trimeric by a secondary mutation in a hydrophobic repeat. No other sequences of hHSF1 appeared to be involved in its heat regulation, except that mutations in carboxy-terminal sequences between amino acids 277 and 529 that include transcriptional activation domains rendered hHSF1 partially or completely inactive (Zuo, J. et al., *Mol. Cell. Biol.*, 14:7557–7568 (1994); Zuo, J. et al., *Mol. Cell Biol.* 15:4319–4330 (1995)).

Overlapping observations were made on hHSF1 expressed in mammalian cells from a transfected hHSF1 gene controlled by a viral promoter, except that the overexpressed hHSF1 was found to be largely trimeric and HSE DNA-binding in the absence of heat shock (Zuo, J. et al., *Mol. Cell. Biol.*, 15:4319–4330 (1995)). The hHSF1 produced was incapable of stimulating the expression of a CAT reporter gene linked to the promoter of a minor, heat-inducible hsp70 gene (hsp70B-CAT). By making use of an appropriate construct encoding the LexA-hHSF1 chimeric factor, it was shown that inactive, trimeric factor was converted to an active factor capable of enhancing transcription from a LexA-CAT reporter gene by heat shock treatment. Deletions or amino acid replacements within the second hydrophobic repeat or sequences beginning immediately adjacent to this repeat (amino acids 203 to 315) rendered hHSF1 capable of enhancing transcription from the hsp70B-CAT reporter gene in the absence of heat shock. For example, deletion of amino acids 186–201, 203–277, or 203–315 activate the factor as do several small three- or seven-residue-long deletions in the residue-186–201 region, or replacements of residues 189, 191 (Zuo, J. et al., *Mol. Cell. Biol.*, 14:7557–7568 (1994)), 279, 298 (Newton, E. M. et al., *Mol. Cell. Biol.*, 16:839–846 (1996)) 290–292 or 307. Simultaneous replacements at positions 303 and 307 have been shown to be more effective than a single substitution at position 307. These and other results define a regulatory region involved in the control of the transcriptional competence of hHSF1, between about amino acid 180 and about amino acid 315. A mutHSF which differs from the wildtype HSF in its amino acid sequences by at least one amino acid residue in the regulatory region is one of the subjects of this invention, as is its use in modulating or altering (e.g., enhancing) hsp synthesis or expression. For example, in embodiments where hsp synthesis is enhanced, one or more amino acid residues in the regulatory region (approximately amino acids 180 to 315 of human HSF, whose sequence is represented in the Figure) are replaced, deleted or modified. In further embodiments, the wildtype HSF regulatory region is modified by addition of one or more amino acid residues. No more than routine experimentation is needed to determine other useful mutants of HSF. Other mutants of HSF having similar effects can be made in this region as described herein.

Genes for HSF have been isolated from different organisms. In common to all HSF are a region encoding an HSE DNA-binding domain and three separate stretches of sequences coding for hydrophobic repeats. Genes encoding a positively-acting mutHSF can be prepared from an HSF gene by mutating a regulatory region defined by reference to the second and third hydrophobic repeats and located from about residues 180 and to about residue 315 in human HSF. Because of the redundance of the third hydrophobic repeat and the substitutability of the transcription activation regions, a mutHSF may be constructed by assembling an HSE DNA-binding domain, an oligomerization domain (the first hydrophobic repeat region), a nuclear localization signal and a functional activation domain.

A negatively-acting mutHSF is a protein that either competes with endogenous HSF for binding to HSE sequences in hsp gene promoters or that is capable of forming heteromeric, nonfunctional complexes with endogenous HSF. As shown herein, any sizeable deletion of sequences between about residue 277 and about residue 529 interferes with or inhibits the function of the carboxy-terminally located activation domains of human HSF1. Thus, a negatively-acting mutHSF can be derived from a HSF by deleting all or a portion of the amino acid sequence of the transactivation domain of the HSF, such that the transactivation activity of the HSF is inhibited. Such negatively-acting mutHSFs bind HSE DNA equally as well as wildtype HSF1. In a cell, overexpressed negatively-acting mutHSF will bind to HSE elements, preventing binding of functional, endogenous HSF activated by stress. Negatively-acting mutants may also be prepared by directed mutation of the activation regions. Based on the conserved nature of HSF from different organisms, a negatively acting mutHSF may be constructed by assembling an HSE DNA-binding domain, an oligomerization domain from an HSF and a nuclear localization signal. A negatively acting mutHSF may also be prepared by removing from an HSF the HSE DNA-binding region. The resulting protein is capable of oligomerizing with endogenous HSF, precluding the assembly of three HSE DNA-binding domains needed for specific DNA binding.

For example, a negatively acting mutHSF (a factor capable of preventing or reducing induction of hsp gene expression by a stressful condition) can be prepared by removal or blockade of the transactivation function from an HSF resulting in a factor that is constitutively HSE DNA-binding but that is incapable of activating promoters with which it interacts. Considering the small amounts of HSF normally present in a cell, a moderate amount of such a mutHSF will compete with endogenous factor for the available HSE binding sites, preventing the endogenous factor from binding to and activating hsp genes. The transactivation domains of animal HSF (vertebrate HSF1) were mapped to the carboxy terminal one third of the amino acid sequence of the factor. Almost any sizeable deletion in this region and an adjacent region (residues 277–529 in human HSF1 and in corresponding regions in other HSFs) results in a transcriptionally inert but DNA-binding factor that will function as a negatively acting mutHSF (Zuo, J. et al., *Mol. Cell. Biol.* 15: 4319–30 (1995)). Another approach to producing a negatively-acting mutHSF is to delete the HSE DNA-binding domain of HSF or to substitute it with a DNA-binding domain from another protein (See Zuo et al., 1995, for LexA-HSF1 chimeras). A single HSE DNA-binding domain is at best weakly capable of binding the HSE sequence. A multimeric binding domain comprised of at least two HSE DNA-binding domains is required for high affinity DNA binding (Harrison, C. J. et al., *Science* 263: 224–7 (1994)). Thus, a mutHSF containing oligomerization and possibly other sequences of HSF but not the HSE DNA-binding domain would, upon introduction into cells in sufficient quantity, form heterooligomers with endogenous factor comprising-no more than one molecule of endogenous HSF (containing an HSE DNA-binding domain) per oligomer. The heterooligomers will be incapable of efficiently binding HSE DNA and of activating hsp genes.

When applications involving upregulation of hsp synthesis are considered, a mutHSF refers to an HSF (a vertebrate, such as a mammalian, particularly human, HSF1) molecule mutated (e.g., deletions, additions, substitutions) in at least one amino acid residue within the regulatory region. Other vertebrate HSF1, as well as HSF from non-vertebrate organisms, can be used in the methods of the present invention because of the conserved nature of the HSE DNA-binding domain and the three hydrophobic domains. These regions can be located readily in any HSF, providing necessary coordinates for the placement of mutations effective in activating the HSF. The finding that single amino acid substitutions in the regulatory region that are far removed from one another activate HSF1 strongly suggests that the substitutions affect the conformation of the regulatory region, and that activation of HSF1 occurs as a result of such a conformation change. Productive conformational changes in the regulatory region can be achieved not only through amino acid substitutions and deletions within the regulatory region, but also from insertion of sequences in the regulatory region or even from the addition of sequences outside of the regulatory region. HSF1 (or HSF) molecules activated by the latter manipulations are considered to be within the scope of this invention. Furthermore, it is known that the transcriptional activation domains in HSF1 can be functionally replaced with activation domains from other transcription factors (Newton, E. M. et al, *Mol. Cell. Biol.*, 16:839–846 (1996)). Finally, it has also been shown in experiments in which factors were synthesized in vitro that removal of the hydrophobic repeat 3 renders HSF3 DNA binding (Nakai, A., and Morimoto, R. I., *Mol. Cell. Biol.*, 13:1983–1997 (1993); Zuo, J. et al., *Mol. Cell. Biol.* 14: 7557–68 (1994)).

In applications requiring hsp upregulation, a functional mutHSF molecule minimally comprises a HSE DNA-binding domain, an oligomerization (trimerization) domain (hydrophobic repeat one) from any HSF, a nuclear localization and a transactivation domain. In applications requiring downregulation of hsp, a functional mutHSF molecule may contain the same elements as positively-acting mutHSF except for the absence of a functional HSE DNA-binding domain or transcription activation domains. Minimally, negatively-acting mutHSF comprises a suitable oligomerization domain of a HSF.

A HSE DNA-binding domain can be obtained from a variety of sources. For example, a HSE-DNA binding domain can be obtained from any HSF, such as human HSF1. In addition, a HSE DNA-binding domain can be obtained from a promoter of a stress-inducible hsp gene (e.g., HSF, HSF1, hsp70, hsp60, hsp90).

An oligomerization, (trimerization) domain can also be obtained from a variety of sources. For example, an oligomerization domain can be obtained from any HSF, such as human HSF1.

A nuclear localization signal for use in the mutHSF of the present invention can be obtained from any suitable source, such as from a transcription factor or a nuclear protein, provided for the embodiments in which positively-acting mutHSF is used, that the nuclear localization signal is appropriate to result in entry of positively-acting or negatively-acting HSF into the nuclei target cell. The nuclear localization signal could also be prepared synthetically, for example, modeled on the SV40 consensus nuclear localization signal (NLS).

A transcription activation domain for use in the mutHSF of the present invention can be obtained from any suitable source, such as the viral protein, VP16, or other transcription factors. Alternatively it may be obtained by screening random sequences for a functional activation domain or may be prepared synthetically, provided that the transactivation domain is functional (i.e., sufficient to cause activation of endogenous hsp gene(s), resulting in enhanced expression of endogenous hsp).

The mutHSF molecule may also include other protein sequences, as long as they do not interfere with transcription factor function, that are not normally associated with an HSF, such as a linker sequence.

The mutHSF gene can be delivered by a variety of approaches, such as in a DNA or RNA vector (e.g., a viral, retroviral or mammalian vector) which is delivered by direct injection into cells, by transfection procedures including calcium phosphate precipitation, lipofection or by means of liposomes, by electroporation, by particle gun or by receptor-mediated uptake. Any other delivery method by which DNA or RNA can be introduced into cells can be utilized.

In the case of gene therapy, a mutHSF-coding sequence is introduced into a suitable vector containing a promoter sequence to drive the expression of mutHSF. The vector may be a plasmid, bacteriophage, plant or animal viral vector, or a DNA capable of replicating or being maintained in the host cells. The vector containing mutHSF is introduced by an appropriate method, e.g., injection, transfection, electroporation, lipofection or infection, into host cells. Host cells may be treated ex vivo and then administered to an individual. Alternatively, the vector may be targeted to a particular tissue or may be administered systemically to an individual.

Alternatively, mutHSF may be delivered as a protein therapeutic. To prepare mutHSF in this case, a mutHSF gene is inserted into a suitable vector using standard molecular biological techniques, and the resulting construct is introduced into producer cells. The producer cells may be bacterial cells, for example, *Escherichia coli*. It is also possible to use fungal, animal or plant cells to produce mutHSF. The person skilled in the art will know how to choose a suitable combination of vector, or viral or other vehicle, and producer cells, as well as how to insert the gene into the vector or vehicle, introduce the vector or vehicle into producer cells and achieve mutHSF expression. Irrespective of the producer cell chosen, mutHSF produced in this manner will form a DNA-binding trimeric structure. Hence, production can be monitored most conveniently by HSE DNA-binding assays, such as mobility shift assays. Alternatively, monitoring may be by western blot analysis of extract samples from producer cells using a specific anti-HSF antibody. In those cases in which a mutHSF from an organism closely related to the producer cells is expressed and immunological cross-reactivity is observed, the mutHSF can be distinguished from endogenous HSF based on the differences in subunit molecular weight, which will be typically lower for the mutHSF than for endogenous HSF by the length of the particular sequence removed to generate the mutHSF. mutHSF can be purified by conventional biochemical methods or by HSE DNA-affinity chromatography (Goldenberg, C. J. et al., *J. Biol. Chem.* 263: 19734–39 (1988)), or by a combination of methods. If non-bacterial cells are utilized as producer cells, preparations may be contaminated by inadvertently activated endogenous HSF that may be difficult to separate from mutHSF. While biochemical methods may be developed to achieve the separation, it may be more convenient to produce mutHSF as an amino terminally tagged protein. Poly-histidine- and Flag-tagged mutHSF were found to be produced as DNA-binding, trimeric proteins. The addition of a tag will allow purification by means of tag-specific affinity chromatography. The tag may or may not be removed subsequently. The transcriptional activity of purified mutHSF may be tested in various ways, including by coinjection (nuclear) with an hsp promoter-driven reporter gene into *Xenopus laevis* oocytes. Transcriptional activity can be scored as reporter gene activity.

Purified mutHSF can be delivered to a target cell(s), tissue or organism by any method suitable for introducing proteins into a cell(s), tissue or organism. For example, mutHSF may be packaged in a liposome for delivery. mutHSF may then be included in a formulation suitable for introduction of the protein into host cells. Host cells may be treated with the formulation ex vivo. Alternatively, the protein formulation may be introduced into a particular tissue or administered systemically.

As described in greater detail in the Examples which follow, Applicant has shown that mutHSF induces endogenous hsp genes. (See Example 2) Briefly, a mutHSF cDNA gene was introduced into an adenovirus 5 vector using routine subcloning procedures; in these particular experiments an hHSF1 gene lacking the region coding residues 203–315 was used. When human HeLa or MRC5 cells were infected with the mutHSF virus, they produced mutHSF, as shown by anti-hHSF1 western blot. Substantial upregulation of hsp90, hsc70, hsp70 (also referred to as hsp72), hsp60 and hsp25 (also referred to as hsp27) was detected at different times, between 15 and 36 hours after infection, by western blots probed with the respective, specific anti-hsp antibodies. Upregulation was also demonstrated by pulse-labeling infected cells with 3H-leucine, followed by SDS-PAGE and fluorography. No increases in hsp expression were detected in cells infected with the viral vehicle alone. Analogous results were obtained when the same mutHSF gene linked to a cytomegalovirus promoter was introduced into cells by lipofection using the commercial Lipofectamine™ reagent. In these experiments, cells were co-transfected with the mutHSF gene and a gene encoding in expressible form a green fluorescent protein (GFP). Successfully transfected cells were isolated by fluorescence activated cell sorting (FACS) based on GFP's fluorescence. The sorted, fluorescent (transfected) cells were shown to contain elevated levels of hsp70 and hsp90 when compared with sorted, non-fluorescent cells. Other hsps were not assayed for in these experiments. When similar experiments were conducted with several different rodent cell lines, a different pattern of hsp overexpression than in human cell types was seen: hsp90 and, to a lesser extent, hsp25 were clearly overexpressed; the rate of hsp70 synthesis was only marginally enhanced.

Upregulation of hsp gene expression by mutHSF results in greater production of hsp (enhanced production) than would occur in the absence of mutHSF and the hsp produced impart a protected state on the cells in which hsp expression is upregulated.

That hsp expressed as a result of the effects of mutHSF provide the protective effects that hsp are generally believed to have, is demonstrated by the experiments described in Example 3. The work described in Example 3 assessed three different aspects of the protected phenotype: resistance to stress-induced cell killing, resistance to stress-induced collapse of the cytoskeletal organization and resistance to cell cycle arrest. Briefly, to investigate the first two aspects, HeLa-CAT cells (HeLa cells with an integrated CAT gene driven by a human hsp70 promoter) were infected with mutHSF virus or, as a control, viral vehicle alone. Cells were then exposed to a 20-min heat shock at 49° C. After overnight incubation at the control temperature (37° C.), cell survival was estimated by scoring vital stain (trypan blue)-excluding cells. Uninfected cells or viral vehicle-infected cells had a 40% survival rate. mutHSF virus-infected cells were 100% protected from hyperthermic killing. Exposure of cells to a lower temperature does not result in their rapid killing, but causes them to reversibly detach from the tissue culture substratum. This detachment was taken as a measure for the temperature-induced collapse of cytoskeletal organization. A 20-min exposure to 47° C. heat caused about 85% of cells to detach from tissue culture dishes. The same was true for cells that had been infected with viral vehicle. In contrast, only 25% of cells infected with mutHSF virus detached. Thus, mutHSF-induced hsp overexpression protected cells against hyperthermic killing and cytoskeletal collapse.

When HeLa-CAT cells were exposed to a one-hour/43° C. heat shock and incubated for 15 hours at 37° C., a large fraction of the cells accumulated in G2/M phase, indicating that the cells were arrested in G2/M phase. This cell cycle arrest was followed by flow cytometry of propidium iodide-stained cells. To determine whether mutHSF-induced expression (enhanced expression) of hsp protects the cells from hyperthermia-induced cell cycle arrest, cells were either co-transfected with a CMV promoter-linked mutHSF gene construct and a GFP construct, or singly transfected with the GFP construct. After heat treatment and postincubation as described herein, cells were sorted based on GFP fluorescence. Cells sorted as positive (containing GFP and mutHSF or, in the control experiment, GFP) and cells sorted as negative were either propidium iodide-stained and subjected to flow cytometry to determine DNA contents or used in western blots to detect mutHSF and hsp70 expression. Results indicated that cells containing only GFP underwent G2/M arrest in a manner similar to that of untransfected cells; in contrast, only a small fraction of cells containing GFP and mutHSF and expressing hsp70 appeared arrested.

Thus, expression of hsps induced by mutHSF appeared to protect cells against hyperthermia-induced cell cycle arrest.

In summary, the experiments presented in Examples 2 and 3 demonstrate that introduction of mutHSF into human cells results in a dramatic upregulation of all major hsps analyzed: hsp90, hsc70, hsp70, hsp60 and hsp25. This upregulation results in protection (partial or complete) of the cells in that they become resistant to heat killing, heat-induced collapse of the cytoskeleton and heat-induced cell cycle arrest.

It is now clear as a result of numerous studies conducted over the course of the last twenty years that preconditioning cells, tissues, organs or organisms with heat renders them resistant to hyperthermic damage from a subsequent severe hyperthermic treatment, i.e., the cells, tissues, organs and organisms acquire a protected phenotype. Acquisition of the protected phenotype correlates with the accumulation of hsps (for a review, see Parsell, D. A., and Lindquist, S., Annu. Rev. Genet. 27: 437–96 (1993)). Furthermore, pretreatment of cells with agents such as ethanol or sodium arsenite is similarly effective in rendering cells resistant to heat killing (Li, G. C., J. Cell Physiol. 115: 116–122 (1983)). These agents have also been shown to induce the accumulation of hsps. Moreover, transfection experiments with hsp70 genes demonstrate that at least part of the protective effect of heat preconditioning against hyperthermic killing can be ascribed to hsp70 overexpression. The experiments in Example 3 on protection against heat killing demonstrate that upregulation of hsp by mutHSF upregulation of all hsp, provides an analogous protective effect as is achieved by upregulation of hsp70 alone. Transfection experiments with hsp25 genes revealed that hsp25 mitigates heat-induced cytoskeletal collapse (Lavoie, J. N., et al., J. Biol. Chem. 268: 3420–9 (1993)). The experiments on heat-induced detachment of cells described in Example 3 showed that upregulation of all hsps also protects cytoskeletal integrity. Thus, expression of all hsps mediated by mutHSF protects against damage that can be mitigated by expression of individual hsps, including specifically hsp70 and hsp25. Accumulation of all hsps induced by mutHSF will be protective in those situations in which overexpression of an individual hsp or a combination of hsps has been found to be effective.

A mutHSF is used in the present invention to modulate hsp gene expression in eukaryotic, particularly mammalian and specifically human, cells as an alternative to chemical modulators (inducers and inhibitors) of hsp gene expression. Modulation of hsp expression can occur ex vivo in cells such as blood or bone marrow cells removed from an individual and manipulated by introduction of mutHSF or DNA encoding mutHSF to enhance or downregulate hsp expression. Cells in which hsp production is modulated can be reintroduced into the individual from whom they were obtained or introduced into another suitable or compatible individual, such as an individual in whom enhanced hsp production is desired. Alternatively, modulation of hsp production can be effected in vivo, such as by introducing into an individual in need of regulation of hsp, exogenous DNA encoding mutHSF in expressible form or mutHSF protein in sufficient quantity and in appropriate compositions for entry of the DNA or protein into cells, in which hsp production is to be modified (e.g., enhanced or reduced), to produce the desired effect (e.g., protection against stress or other adverse condition or targeting of selected cells for immune recognition or killing by a stress).

Regulation of hsp synthesis is linked to and is in fact controlled by the intracellular concentration of nonnative protein (Ananthan, J. et al., Science 232:522–524 (1986)). Inducers of hsp synthesis appear to stimulate hsp expression as a consequence of their ability to cause denaturation of cellular proteins (Ananthan, J., et al., Science 232:522–524 (1986)). Thus, hsp synthesis is only induced by chemical inducers in cells that are stressed to the point at which a fraction of the cellular protein is being denatured. Inhibitors of hsp gene expression (e.g., certain inhibitors of Ser/Thr protein kinases including H7, staurosporine, GF-X, and calphostin and of Tyr protein kinases such as quercetin) are also cytotoxic presumably because of their profound effects on normal signal transduction. Modulation of hsp expression by mutHSF, administered as mutHSF protein or as mutHSF-encoding DNA, does not suffer from these complicating factors, which may be unacceptable in certain medical circumstances, since mutHSF is a native protein with a specialized function whose only effect in a therapeutic setting is to bypass normal regulation of hsp gene expression. Thus, in these circumstances, it will be preferable to modulate hsp synthesis through the introduction into cells of mutHSF (or mutHSF-encoding DNA), rather than through administration of cytotoxic chemical inducers and inhibitors.

Some of the same advantages may be gained by hsp or hsp gene therapy, in which one or more hsp or one or more genes encoding hsp are introduced into cells. While many beneficial effects of hsp modulation can be ascribed to hsp70, some appear to be due to other hsps. For example, there is a growing appreciation that protection of the CNS from ischemic and reperfusion damage may be achieved in part through upregulation of hsp25, and hsp25 has been shown to be involved in drug resistance, resistance to oxidative stress and in protecting the cytoskeleton. Therapy with mutHSF should, therefore, be more generally useful than hsp therapy, since mutHSF therapy will allow the simultaneous modulation of the levels of all hsps.

Examples of applications in which upregulation of hsp synthesis by positively-acting mutHSF will be beneficial include chemotherapy situations in which it is desired to shield cells, tissues, and organs that are not targets of the therapy from the cytotoxic side effects of the chemotherapeutic agent. The feasibility of these applications are based on the following observations: overexpression of hsp25 in human testis tumor cells by introduction of a functional hsp25 gene resulted in increased resistance of the cells to heat, cis-platinum and the anthracyclin doxorubicin (Richards, E. H. et al., Cancer Res. 55: 2446–51 (1996)). Furthermore, expression of hsp25 in human breast cancer cell lines was found to correlate with resistance to the drug doxorubicin and to heat (Oesterreich, S. et al., Cancer Res. 53: 4443–4448 (1993)). Transfection of underexpressing breast cancer cell lines with an hsp25 gene rendered them resistant to doxorubicin (Mahvi, D. M. et al., Endocrine 4: 269–275 (1996)). In addition, overexpression of hsp70 was reported to overcome the G2/M cell cycle arrest induced by doxorubicin (Karlseder, J. et al., BBRC 220: 153–9 (1996)). Heat preconditioning of testis and bladder cancer cells increased their resistance to doxrubicin, but not to cis-platinum (Richards, E. H. et al, Int. J. Oncol. 8: 1265–71 (1996)). Moreover, cross-resistance to adriamycin was observed in Chinese hamster fibroblasts selected for heat resistance (Wallner, K., and Li, G. C., Oncol. Biol. Physiol. 12: 829–33 (1986)). Finally, overexpression of hsp70 in WEHI-S fibrosarcoma cells rendered them resistant against two new anticancer drugs, gemcitabine and topotecan (Sliutz, G. et al., Br. J. Cancer 74: 172–7 (1996)).

Positively-acting mutHSF may also be used to protect cells, tissue and organs from hyperthermic and oxidative damage, damage from exposure to noxious chemicals, to inflammatory cytokines, from sepsis, and from UVB light. The following observations provide the rationales for these applications: Transfection experiments with hsp70 and hsp90 genes demonstrated that overexpression of either hsp90 or hsp70 protects neuronal cells against heat killing (Mailhos, C. et al., *J. Neurochem.* 63: 1787–95 (1994)). Rat cells transfected with a human hsp70 gene (Liu, R. Y. et al., *Cancer Res.* 52: 3667–73 (1992)) and rat cell lines overexpressing human hsp70 (Li, L. et al., *Exp. Cell Res.* 217: 460–8; see also Li, G. C. et al., *Proc. Natl. Acad. Sci., USA* 89: 2036–40 (1992)) were found to have increased resistance to heat-induced inhibition of transcription, translation and thermal killing, when compared to the respective naive cell lines.

Chinese hamster fibroblasts preexposed to sublethal heat (which induces hsp synthesis) or sublethal levels of the oxidative stressor hydrogen peroxide show increased resistance to oxidant stress (Spitz, D. R. et al., *J. Cell Physiol.* 131: 364–73 (1987)). Chinese hamster fibroblasts exposed to the sulfhydryl reagent cysteamine that induces oxidative stress develop thermotolerance and express increased levels of hsps (Issels, R. D. et al., *Cancer Res.* 47: 2268–74 (1987)). Further, heat treatment of mice by means of an amphetamine dose protects their livers against bromobenzene and acetaminophen.

By expression of a human hsp70 gene in TNF-sensitive WEHI-S cells, it was shown that expression of excess hsp70 renders the cells resistant to TNF cytotoxicity (Jaattela, M. et al., *EMBO J.* 11: 3507–12 (1992)). Another study demonstrated in a mouse cell culture assay that overexpression of hsp25 increases glutathione levels which increase is of importance in protecting the cells against TNFalpha and oxidative stressors (Mehlen, P. et al., *EMBO J.* 15: 2695–706 (1996)). A second study with cultured murine cells corroborated these findings (Wang, G. et al. *J. Immunotherap.* 19: 9–20 (1996)).

TNF is an important mediator of sepsis. To test whether upregulation of hsps could protect against sepsis in a whole animal model, Hotchkiss et al. subjected mice to transient whole body hyperthermia and found that this pretreatment protected the mice against endotoxin challenge. (Hotchkiss, R. et al., *Am. J. Physiol.* 265: 1447–57 (1993)) This protective effect correlated with the expression of hsps. Similar conclusions were reached by Villar et al. working with a rat model of intra-abdominal sepsis and sepsis-induced acute lung injury produced by cecal ligation and perforation (Villar, J. et al., *Crit. Care Med.* 22: 914–21 (1994)). Interestingly, sodium arsenite, an inducer of hsp72 in the lung, was effective in reducing mortality in the same lung sepsis model (Ribeiro, S. P. et al., *Crit. Care Med.* 22: 922–9 (1994)). Pathologic vasodilation is a characteristic aspect of sepsis, and nitric oxide (NO) is thought to be involved in this process. Stewart et al. (Stewart, T. E. et al., *Am. J. Respir. Crit. Care Med.* 151: 713–8 (1995)) showed, using their rat lung sepsis model, that septic animals have greatly increased exhaled concentrations of NO. As discussed below, NO production is inhibited by hsps, particularly by hsp72.

The UVB resistance of epidermal carcinoma cell line A431 can be increased significantly by heat preconditioning. Exposure of cells to an antisense oligonucleotide to hsp72 or to quercetin, an inhibitor of the heat shock response (Hosokawa, N. et al., *Cell Struct. Func.* 15: 393–401 (1990)), sensitizes cells to UVB damage (Trautinger, F. et al , *J. Invest. Dermatol.* 105: 160–2 (1995)). Overexpression of hsp70 in murine fibrosarcoma cells (WEHI-S) increases their viability when exposed to UVB light. Hsp72 appears to mitigate the oxidative stress caused by UV irradiation. Interestingly, it also downregulates the release of pro-inflammatory cytokines such as IL1 and IL6 (Simon, M. M. et al., *J. Clin. Invest.*95: 926–33 (1995)).

Ischemic damage, typically resulting from an interruption in the blood flow or from severe acute or chronic limitation of blood flow and aggravated by oxidative damage caused during reperfusion following the ischemic event, is a medical problem of large dimension. This type of problem occurs acutely during heart failure or chronically in certain heart conditions. It may also occur as a consequence of surgery, especially with elderly patients. Damage caused during angioplastic procedures that results in inflammatory responses and frequently restenosis, may also be related. Strokes, trauma and, perhaps, also certain chronic conditions, cause ischemia in the brain. Ischemic complications may occur during aortic and brain surgery. Various other tissues, such as the aorta, the vasculature, as well as kidney, liver and the intestinal system are also susceptible to ischemic damage as a consequence of injury and surgery. Based on the observations presented below, application of positively-acting mutHSF will be beneficial to mitigate the damaging effects of ischemic and reperfusion events.

Ischemia is a multifaceted event. There is direct damage at the cellular level produced by depletion of oxygen and other changes in the tissue milieu. This process can be studied in cell culture models simulating ischemia. It was demonstrated in such a model that hsp, particularly hsp70, protect against direct ischemic damage (Mestril, R. et al., *J. Clin. Invest.* 93: 759–67 (1994)). Herbimycin A was reported to specifically induce hsp72 in cardiomyocytes, resulting in cytoprotection (Morris, S. D. et al., *Circulation* 92: 1–652 (1995)).

A second aspect of ischemia is a profound inflammatory response. Again, overexpression of hsp, particularly hsp70, mitigates against both the elicitation of this response and the damage caused by it. Mitigation of inflammatory reactions and their consequences by hsp overexpression was studied in various tissue culture models. Heat preconditioning as well as overexpression of hsp70 from a transfected gene protects rat islet cells (rat insulinoma cell line RINm5F) against NO toxicity (Bellmann, K. et al., *FEBS Lett.* 391: 185–8 (1996)). It has long been known that accumulation of nonnative protein induces hsp synthesis (Ananthan, J. et al., *Science* 232: 522–4 (1986)). One would expect that unfolded proteins would accumulate if the proteasome pathway is inhibited. Indeed, it was observed that addition of specific proteasome inhibitors to cells caused upregulation of hsp72 transcription (Zhou, M. et al., *J. Biol. Chem.* 271: 24769–75 (1996)). It was recently reported that proteasome inhibitors interfere with NFκB activation and the induction of NO synthase in macrophages (Griscavage, J. M. et al., *Proc. Natl. Acad. Sci., USA* 93: 3308–12 1996)). Together the two observations suggest that an hsp, most probably hsp72, blocks the activation of transcription factor NFκB that regulates NO synthase expression and various other aspects of the immune response that depend on NFκB activation. Feinstein et al. showed more directly that heat shock or transfection of an hsp70 gene inhibits NO synthase expression in brain glial cells. Evidence was provided that hsp70 interferes with the activation of NFkB by LPS or pro-inflammatory cytokines by inhibiting the nuclear translocation of the factor (Feinstein, D. L. et al., *J. Biol. Chem.* 271: 17724–32 (1996)). By expressing a human hsp70 gene in TNF-sensitive WEHI-S cells, it was shown that expression of excess hsp70 renders the cells resistant to TNF cytotoxicity (Jaattela, M. et al., *EMBO J.* 11: 3507–12

(1992)). This resistance may be explained by the observation that elevated levels of hsp70 interfere with the activation of phospholipase A2 (Jaattela, M., *J. Immunol.* 151: 4286–94 (1993)). Another study demonstrated in a mouse cell culture assay that overexpression of hsp25 increases the glutathione levels which is of importance in protection against TNFalpha and oxydative stressors (Mehlen, P. et al., *EMBO J.* 15: 2695–706 (1996)). Another event occurring in ischemic brain and leading to nerve cell damage is the release and failure to reabsorb glutamate. Glutamate stimulates non-NMDA receptors, causing depolarization of the membrane and sodium and calcium permeability. As a consequence, NO synthase expression is increased, causing the concentration of NO to rise to a toxic level. Grilli et al. recently reported that aspirin and sodium salicylate protect neural cells against glutamate-induced cell death (Grilli, M. et al., 1996). While salicylate typically only induces the DNA-binding ability of HSF (Jurivich, D. A. et al., *J. Biol. Chem.* 270: 24489–95 (1995)), salicylate in combination with a drug that increases HSF phosphorylation can fully activate the factor to stimulate hsp gene expression (Xia, W., and Voellmy, R. 1997 *J. Biol. Chem.,* 272:4094–4102 (1997)). It can, therefore, be reasonably expected that salicylate in combination with receptor activation by glutamate activates HSF, triggering the accumulation of hsp. This interpretation is consistent with the finding reported by Grilli et al. that salicylate prevents NFκB activation and the prior observation that NFκB activation is blocked by hsp70. Thus, overexpression of hsp may also mitigate glutamate toxicity in the ischemic brain. A further aspect of ischemia known to significantly contribute to inflammatory processes is damage caused upon reperfusion of tissues and organs subsequent to an ischemic event. Reperfusion causes a buildup of reactive oxygen species, i.e., induces oxidative stress. Exposure of peripheral blood lymphocytes to hydrogen peroxide or to xanthine oxidase plus hypoxanthine, generating free radicals, was reported to induce a set of hsps including heme oxygenase I and to precondition the cells to withstand subsequent challenges by reactive oxygen species. Heat shock pretreatment had a similarly protective effect (Marini, M. et al., *Int. J. Radiat. Biol.* 70: 337–350 (1996)).

The ability of hsp to protect against ischemic damage in tissues and organs was demonstrated by heat preconditioning experiments (reviewed in Richard, V. et al., *Fund. Clin. Pharmacol.* 10: 409–15 (1996)) as well as by studies with transgenic animals. Hearts of transgenic mice overexpressing hsp70 were subjected to an ischemic event. Recovery of hearts from ischemic trauma were assessed following 30 min of reperfusion after the ischemic event. As judged from measurements of contractile force and creatine kinase release, hearts from transgenic mice showed significant improvement of recovery when compared to hearts from nontransgenic animals (Plumier, J. C. et al., *J. Clin. Invest.* 95: 1854–60 (1995)). These results were corroborated by a second, similar study also using hsp70 transgene-expressing mice (Marber, M. S. et al., *J. Clin. Invest.*95: 1446–56 (1995)). The purposeful induction of hsp by chemical inducers was also found to protect organs to be used in transplantation from ischemic and reperfusion damage (Perdrizet, G. A., *New Horiz.* 3: 312–20 (1995)).

Thus, the present invention relates to a method of enhancing synthesis of hsp in an individual comprising administering to the individual positively-acting HSF in a quantity sufficient and under conditions appropriate for the mutHSF to be introduced into cells of the individual and enhance hsp synthesis. In another embodiment, the invention relates to a method of inducing a protected state in the cells of an individual in need thereof (e.g., to protect the individual's cells from chemotherapy, UVB, sepsis, ischemia), comprising administering to the individual a positively-acting mutHSF in a quantity sufficient and under conditions appropriate for the mutHSF to be introduced into cells of the individual and enhance hsp synthesis, thereby producing a protected state.

Positively-acting mutHSF can also be applied to cancer immunotherapy. Hsps are very highly conserved proteins and are known to be dominant antigens in a broad spectrum of pathogens and in autoimmune disease (Young, R. A., *Annu. Rev. Immunol.* 8:401–420 (1990)). Hsp90 has long been recognized as a tumor rejection antigen of murine sarcomas (Ullrich, S. J. et al., *Proc. Natl. Acad. Sci., USA* 83: 3121 (1986)). Stress-inducible hsp70 was shown to be a cell surface-expressed tumor-associated antigen of a H-ras oncogene-transformed rat fibrosarcoma line. The cytotoxicity of CD4-CD8-T cells against the tumor cell but not the parent cell could be abrogated by anti-hsp70 antibody (Tamura, Y. et al., *J. Immunol.* 151: 5516–24 (1993)). The same researchers reported in a more recent article that the cytotoxic reactions are likely directed to a complex of hsp70 and a peptide (Takashima et al. *J. Immunol.* 157: 3391–5 (1996)). A study with human sarcomas also showed the presence of an inducible hsp70 molecule on the cell surface of transformed cells but not of normal cells (Multhoff, G. et al., *Blood* 86: 1374–82 (1995)). Human gamma delta T cells recognize a defined (tumor) antigen on a human lymphoblastoid cell line in the context of a member of the hsp70 family, grp75, and not of classical MHC molecules. These observations suggest that an hsp70 protein plays a critical role in T cell recognition and antigen presentation (Kim, H. J. et al., *J. Immunol.* 154: 1614–23 (1995)). Together these findings show clearly that hsp can be expressed on the surface of mammalian tumor cells and can serve as targets for cytolytic immune reactions.

Several studies have been conducted to show that the deliberate upregulation of hsp in a tumor cell results in its increased immunogenicity, providing the rationale for a cancer therapy approach based on upregulation of hsp. By means of upregulating hsp72 expression by heat shock combined with anti-hsp70 antibody blockade, Multhoff et al. were able to correlate hsp70 surface expression on certain cell lines with increased sensitivity to IL2-stimulated CD3-natural killer cells. Note that in this as well as other studies claiming hsp70 surface expression all that was shown was anti-hsp70 antibody recognition of a surface element. This element may be full length hsp70, an hsp70 fragment, or a peptide derived from the hsp70 sequence. Using a rat colon carcinoma model, Menoret et al. (Menoret, A. et al., *J. Immunol.* 155: 740–747 (1995)) isolated different cell clones from the same tumor and found that the tumorigenic potential of clones in immunocompetent syngeneic animals correlated with their ability to express induced hsp70. A variant was obtained from a highly tumorigenic clone by repeated sublethal heat shock treatments that showed an increased capacity for hsp70 synthesis and decreased tumorigenicity. Conversely, a variant obtained from a regressive clone by in vivo growth in partially immunosuppressed rats acquired tumorigenicity and lost the ability to synthesize induced hsp70. In this study, hsp70 was not detected on the cell surface. Autologous tumor killing is an important prognostic factor in cancer patients since the ability of blood lymphocytes to kill freshly isolated autologous tumor cells is strongly associated with good prognosis of the patients. Wei et al. found that brief heat shock treatment of freshly isolated tumor cells increased their susceptibility to lysis by autologous blood lymphocytes (Wei, Y. et al., *Cancer Res.* 56: 1104–10 (1996)). Western blot analysis revealed increased expression of hsp70 within and on the surface of treated tumor cells. Cytotoxicity of blood lymphocytes was inhibited by treatment of the target tumor cells with an anti-hsp70 antibody. These findings demonstrate that upregulation of an hsp (hsp70) in a tumor cell increases its immunogenicity and, thus, its susceptibility to immune destruction. Such upregulation can be mediated by positively-acting mutHSF introduced into tumor targets as a protein or gene therapeutic. Thus, the present invention relates to a method of increasing the immunogenicity of a tumor cell comprising administering to the individual positively-acting mutHSF in a quantity sufficient and under conditions appropriate for the mutHSF to be introduced into cells of the individual, thereby enhancing hsp synthesis in the tumor cell.

Immunization against and regression of experimental cancers using hsp gene therapy has been achieved, which is supportive of the use of a mutHSF gene therapy approach in treating cancers. A mycobacterial hsp60 gene was introduced by retroviral transfer in cells of the tumorigenic macrophage line J774. Mice injected i.p. with hsp60-expressing J774 cells did not develop tumors, nor did a subsequent challenge with J774 cells result in tumors (Lukacs, K. V. et al., *J. Exp. Med.* 178: 343–8 (1993)). Furthermore, i.p. application of a liposome formulation containing the same hsp60 gene resulted in regression of a preexisting tumor (Lukacs, K. V. et al., *Gene Therapy*, April 1997). Similar observations were made with a mouse melanoma tumor model and a different mycobacterial hsp60 gene (Schweighoffer, T., *Eur. J. Immunol.* 26: 2559–64 (1996)).

Negatively acting mutHSF can be utilized in situations, such as in cancer treatment, in which blocking induced hsp synthesis would be beneficial. As discussed before, hsp provide protection against certain chemotherapeutic drugs. Given the protective role of overexpression of hsp, it is expected that the induction of hsp synthesis by certain drugs reduces their effectiveness. Prevention of this induction will render the cells more sensitive to the drugs, allowing for a more effective treatment and/or for a treatment at reduced drug doses. Prevention of hsp synthesis by a negatively acting mutHSF will also sensitize cells to heat killing. This sensitization should increase the rate of success of hyperthermic cancer therapy. Demonstration of this principle has been provided by a study by Sliutz et al. (Sliutz, G. et al., *Br. J Cancer* 74: 172–7 (1996)) in which hsp70 was shown to render cells resistant to two chemotherapeutic agents and quercetin, an inhibitor of HSF activity (Hosokawa, N. et al., *Cell Struct. Funct.* 15: 393–401 (1990)), to reverse the effect of hsp70 overexpression.

In another approach to cancer treatment, tumor cells may be induced to apoptose by modulating hsp70 expression (Wei, Y.-Q. et al., *Cancer Immunol. Immunotherap.* 40: 73–8 1995)).

In the present invention, mutHSF protein or a gene encoding mutHSF is introduced into target cells in amounts sufficient to cause significant modulation of hsp synthesis in the target cells. The dosage of protein or DNA will depend on the delivery vehicle chosen and on whether mutHSF is intended to be introduced systemically or in a particular tissue. Furthermore, in certain applications, it will be desirable that all target cells receive mutHSF protein or mutHSF DNA, whereas in other applications, for example in protocols designed to elicit an immune response to cancer cells overexpressing hsps, it may be appropriate for only a fraction of cancer cells to receive mutHSF.

In general, dosage can be estimated in many instances based on known characteristics of the chosen delivery vehicle. In other cases, animal model studies can be conducted to determine an appropriate dose range to be used to estimate an effective dose for humans. The dose range in animals may be determined based on effectiveness in relieving the symptom of interest. Alternatively, biopsies may be taken, and the effective dose can be defined as the dose that significantly changes hsp expression. Changes in hsp expression may be detected by any suitable method, including immunohistochemistry or western blots of tissue extracts using commercial antibodies against different hsp, hybridization approaches to detect hsp mRNAs, etc. The correct dosage for a particular application, as well as the number of doses to be given, is ultimately determined in the clinical trial setting.

The present invention is illustrated by the following Examples, which are not intended to be limiting in any way.

EXEMPLIFICATION

Methods

Cell Culture, Plasmids, Transfections, Viral Vectors, and FACS

Human HeLa cells, HeLa-CAT cells (Baler, R. et al., *J. Cell Biol.*, 117:1151–1159 (1992)) containing copies of a human hsp70B promoter-driven chloramphenicol acetyltransferase (CAT) gene or 293 cells were cultured in Dulbecco's modified Eagles' medium (DMEM) supplemented with 10% fetal bovine serum (FBS) in a humidified 5% $CO_2$ atmosphere at 37° C. Human HepG2 cells were cultured in Earle's salt-based MEM supplemented with 10% FBS and 1 mM sodium pyruvate.

Expression plasmids were derived from pcDNA1 or pcDNA3 (Invitrogen Corp., Carlsbad, Calif.) by insertion of cDNA genes for human HSF1 (HSF1(wt)), $LexA_{87}$-human $HSF1_{79}$ (LexA-HSF1(wt)), human HSF1d202–316 (HSF1 (+)), $LexA_{87}$-human $HSF1_{79}$d202–316 (LexA-HSF1(+)), human HSF1d453–523 (HSF1(−)), and bacterial beta-galactosidase as described previously (Zou, J. et al., *Mol. Cell. Biol.*, 15:4319–4330 (1995); Zou, J. et al., *Mol. Cell. Biol.*, 14:7557–7568 (1994)). Construction of reporter plasmid LexA-CAT containing a CAT gene under the control of a minimal promoter supplemented with multiple LexA binding sites was also reported previously (Zou, J. et al., *Mol. Cell. Biol.*, 15:4319–4330 (1995)). Plasmid EGFP-C1 (referred to herein as EGFP), containing a coding sequence for enhanced green fluorescence protein, was obtained from Clontech Laboratories, Inc. (Palo Alto, Calif.). Cells (>70% confluent cultures) were transfected by Lipofectamine™ (Gibco BRL, Life Technologies, Grand Island, N.Y.), using the procedure suggested by the manufacturer.

Recombinant adenovirus vectors were generated by co-transfection of human 293 cells with plasmid AC CMV pLpA SR(+) containing or not containing human HSF1d202–316 (Zou, J. et al., *Mol. Cell. Biol.*, 15:4319–4330 (1995); Zou, J. et al., *Mol. Cell. Biol.*, 14:7557–7568 (1994)) and the infectious plasmid JM17 according to the protocol of Graham and Prevec (Graham, F. I. and Prevec, L., "Manipulation of adenovirus vectors", In: *Methods in Molecular Biology, Vol. 7: Gene Transfer and Expression Protocols* (Murray, E. J., ed.), The Humana Press Inc., Clifton, N.J., pp. 109–127 (1991)). Viral plaques were isolated, expanded, and viral DNA was analyzed by restriction enzyme digestion. Human cell (HeLa-CAT or HepG2)

cultures (>than 70% confluent) were infected at a multiplicity of infection (MOI) of 5–10 PFU/cell.

For fluorescence-activated cell sorting, cells from cultures transfected or co-transfected with EGFP-expressing construct were removed from tissue culture dishes by treatment with 0.04% EDTA in phosphate-buffered saline (PBS) and were resuspended in PBS. Cell suspensions were then applied to a FACStar Plus (Becton-Dickinson, San Jose, Calif.) machine. Excitation wavelength was 488 nm, and detection wave lengths were 650 nm (long pass) for propidium iodide and 520 nm (narrow band) for detection of EGFP fluorescence. For analyses of cell cycle distribution, cells were fixed during at least 18 hours with 70% ethanol and stained with 50 μg/ml propidium iodide (Molecular Probes, Eugene, Oreg.).

Cell Survival/Killing and Detachment Assays, and Simulated Ischemia

After heat treatment, cultures were incubated overnight at 37° C. When trypan blue exclusion was used as the criterion for cell survival, cells (unattached and attached) were harvested, and trypan blue-excluding cells were counted in a hemocytometer. In some experiments, cell killing was estimated by the lactate dehydrogenase (LDH) release assay, using the LDH Assay Kit from Sigma Corp. (St. Louis, Mo.). To quantify detachment from the substratum, cultures were washed three times with prewarmed DMEM, and the number of cells remaining on dishes were determined using a hemocytometer. In the experiment shown in Table 3, cells were fixed in 2% formaldehyde and 0.2% glutaraldehyde in phosphate-buffered saline and stained with X-Gal Reagent (Invitrogen Corp., Carlsbad, Calif.). Ischemic conditions were simulated as described previously (Mestril, R. et al., *J. Clin. Invest.*, 93:759–767 (1994)). Briefly, cells were placed in slightly hypotonic HBSS (1.3 mM $CaCl_2$, 5 mM KCl, 0.3 mM $KH_2PO_4$, 0.5 mM $MgCl_2$, 0.4 mM $MgSO_4$, 69 mM NaCl, 4 mM $NaHCO_3$, 0.3 mM $Na_2HPO_4$) without glucose or serum, and made hypoxic for 4–6 hours at 37° C. Control cells were left under normoxic conditions for the same period of time. Hypoxia was achieved by using an air-tight jar from which oxygen was removed by displacement with argon. After 10 minutes of gas exchange, the oxygen concentration was <0.2%. Hypoxia was maintained using the oxygen-consuming GasPak System from BBL Microbiology Systems (Cockeysville, Md.).

Translational Recovery Experiments

In a typical experiment, parallel HeLa-CAT cultures in 60 mm dishes (more than 70% confluent) were transfected with 0.75 ug of EGFP construct and 2.25 ug of HSF1(+) or HSF1(−) construct and 15 ul Lipofectamine™. Before exposing the cultures to heat shock about 36 hours post transfection, cells were replated (to achieve about 70% confluence). Note that in some experiments, HSF1(+) was delivered by infection with an adenoviral vector rather than by transfection. Cultures were exposed to a 42° C./1 hour heat shock and then returned to 37° C. Rates of protein synthesis before, during, and at different times after a subsequent, more severe heat shock were determined by pulse-labeling of cells with $^3$H-leucine. For labeling, cultures were washed two times with prewarmed PBS, and one ml of labeling medium (leucine-free DMEM with 2% FBS and 65 uCi of $^3$H-leucine (179 Ci/mmolc)) was added. Cultures were incubated for 30 minutes at 37° C., washed two times with PBS, and cells scraped off, collected and lysed in buffer C (20 mM Hepes, 0.42 M NaCl, 1.5 mM MgCl2, 0.2 mM EDTA, 0.5 mM dithiothreitol, 0.5 mM PMSF, 25% glycerol). Aliquots of lysates were used for protein determinations by the Bradford method (Bradford, M. A., *Analytical Biochemistry*, 72:248–254 (1976)) and for precipitation with 10% trichloroacetic acid to measure incorporation of radiolabel into proteins. Relative rates of protein synthesis were calculated as cpm/ug protein. In some experiments, aliquots were also compared by SDS-PAGE and fluorography.

Western Blots

Cells were scraped of dishes and lysed in buffer C. Aliquots containing equal amounts of cell protein as well as prestained molecular weight markers were applied to 8.5% SDS-PAGE gels. Following electrophoresis, proteins were transferred to Immobilon-P Transfer Membranes (Millipore Corp., Bedford, Mass.), and membranes were blocked by incubation with TBS (25 mM Tris-HCl, pH 8.0, 0.136 M NaCl, 2.7 mM KCl) with 2% nonfat dry milk. Appropriate sections of membranes were incubated with anti-HSF1 polyclonal antibody (Baler, R. et al., *Mol. Cell. Biol.*, 13:2486–2496 (1993)), anti-Hsp antibodies (all from StressGen Biotechnologies Corp., Victoria, B C) or anti-actin antibody (Amersham, Arlington Heights, Ill.). Following three washes with TBS, membranes were reblocked and incubated with second antibody (horseradish peroxidase-conjugated anti-mouse or anti-rabbit IgG (Amersham). After several washes in TBS, membranes were developed using the ECL Western Blot Detection Kit (Amersham).

Other Assays

CAT assays were performed using the chromatographic assay of Gorman, C. M. et al., *Mol. Cell. Biol.*, 2:1044–1051 (1982)). DNA replication was assessed by a standard $^3$H-thymidine incorporation assay. In most experiments, including all western blot assays, standardization was based on protein content. All protein determinations were made using the Bradford method. In a few experiments involving sorted cells, standardization was based on cell numbers. All experiments were repeated at least twice, and, in most cases, each data point was derived from assays of 3–5 parallel samples.

Example 1

HSF(−) Prevents Stress-Induced Hsp Expression and the Establishment of a Tolerant State Two previously characterized HSF1 deletions were selected as potential positively and negatively acting factors. HSF1d202–316, also referred to herein as mutHSF or HSF1 (+), expressed from transfected genes is constitutively trimeric and DNA binding and is capable of transactivating an hsp70B promoter-driven reporter gene in the absence of stress (Zou, J. et al., *Mol. Cell. Biol.*, 15:4319–4330 (1995)). HSF1d453–523, referred to below as HSF1(−), is also DNA-binding but lacks functional transcription activation domains (Zou, J. et al., *Mol. Cell. Biol.*, 15:4319–4330 (1995)). Genes for the mutant factors were delivered to cells either by infection with an adenoviral vector (MOI of 5–10) or by Lipofectamine™ transfection. In some experiments, transfection mixtures also included a gene encoding a highly florescent green fluorescent protein (EGFP), and when transfection of most cells was deemed important, EGFP-fluorescing cells isolated by fluorescence-activated cell sorting (FACS) were employed.

To find out whether HSF1(−) could function as a negatively acting factor, HeLa-CAT cells containing integrated copies of an hsp70B-chloramphenicol acetyltransferase (CAT) gene were co-transfected with an HSF1(−) and an EFGP-expressing construct. One day later, cells were subjected to a 41° C./1 hour heat shock and incubated overnight at 37° C. CAT assays on FACS-isolated populations of cells containing or not containing HSF1(−) showed that HSF1(−) severely inhibited heat-induced reporter expression. The factor also greatly reduced heat-induced Hsp accumulation, as demonstrated by anti-Hsp72 western blot. To determine whether elevated Hsp levels induced by heat preconditioning are required for development of tolerance measured as an increased rate of recovery from heat-induced translational arrest, cultures co-transfected with EGFP- and HSF1(−)-expressing constructs or transfected with EGFP-expressing construct only (control cultures) were mildly heat-preconditioned (41° C./1 hour) and, 3 hours later, subjected to a 44° C./30 minutes (severe) heat shock. To allow for recovery, cultures were then incubated at 37° C. for various lengths of time. Rates of protein synthesis were assessed by pulse-labeling cells with $^3$H-leucine. Results from two independent experiments are shown in Table 1.

TABLE 1

RECOVERY OF TRANSLATION AFTER HEAT SHOCK OF HEAT-PRECONDITIONED CELLS

RELATIVE INCORPORATION OF $^3$H-LEUCINE

| PLASMIDS | Before HS | During 2nd HS (44° C./30 min.) | Recovery 1 hour | Recovery 1 hour |
|---|---|---|---|---|
| | | EXPERIMENT 1 | | |
| None | 100 | 7 +/− 1 | 39 +/− 13 | |
| EGFP | 96 +/− 4 | 9 +/− 4 | 33 +/− 2 | 33 |
| EGFP/ HSF1(−) | 104 +/− 3 | 4 +/− 0 | 18 +/− 3 | 5 |
| | | EXPERIMENT 2 | | |
| None | 100 | 4 +/− 1 | 60 +/− 3 | |
| EGFP | 104 +/− 1 | 4 +/− 1 | 60 +/− 3 | 60 |
| EGFP/ HSF1(−) | 98 +/− 9 | 4 +/− 1 | 41 +/− 3 | 24 |

In the first experiment, the rate of protein synthesis dropped to below 10% during heat shock and, in preconditioned control cells, recovered to about 33% one hour after heat shock. In cultures that had been transfected with the HSF1(−) construct, the rate of protein synthesis after the same recovery period was only 18%. In the second experiment, the rate of translation recovered to 63% in cells lacking HSF1(−), but only to 44% in cells expressing HSF1(−). In the absence of preconditioning, the rate of translation after a one hour recovery period was below 5%. These results demonstrated that recovery from translational arrest was substantially reduced in HSF1(−)-expressing cells compared with control cells. Because of the large numbers of cells needed in this type of experiment (and the subsequent experiment), FACS isolation of successfully transfected cells was omitted. To remove the contribution of cells that had not received the HSF1(−) construct from the rates of protein synthesis determined with cultures transfected with the HSF1(−) construct, transfection efficiency was determined cytometrically and was found to be about 53%. Subtraction of the contribution of untransfected cells revealed corrected rates of protein synthesis for HSF1(−)-expressing cells one hour after heat shock of about 5% and 24%, respectively, for the two experiments. To learn whether Hsp accumulation induced by a stressful event is protective during the same event, EGFP/HSF1(−)-und EGFP-transfected (control) cultures were heat-shocked (42° C./1 hour), and recovery from translational arrest was compared 2 hours after heat shock.

TABLE 2

RECOVERY OF TRANSLATION AFTER HEAT SHOCK

RELATIVE INCORPORATION OF $^3$H-LEUCINE

| PLASMIDS | Before HS | During HS 42° C./1 hour | Recovery 2 hours | Recovery 2 hours |
|---|---|---|---|---|
| NONE | 100 | 2 +/− 0 | 63 +/− 6 | |
| EGFP | 105 +/− 6 | 2 +/− 0 | 63 +/− 4 | 63 |
| EGFP/ HSF1(+) | 97 +/− 9 | 2 +/− 0 | 93 +/− 13 | 100 |
| EGFP/ HSF1(−) | 103 +/− 10 | 2 +/− 0 | 44 +/− 6 | 27 |

EGFP-transfected cells recovered significantly better than EGFP/HSF1(−) co-transfected cells. After correction for the presence of untransfected cells was made, the rate of protein synthesis in HSF1(−)-containing cells was found to be only 27% of the rate of not-heat-treated cells, whereas the rate in control cells was restored to about 63% at the end of the 2-hour recovery period. To also assess the effect of expression of HSF1(−) on stress-induced cell killing, cultures were transfected with a beta-galactosidase gene or co-transfected with the beta-galactosidase gene and the HSF1(−) construct.

TABLE 3

CELL SURVIVAL AFTER HEAT-SHOCK (48° C./10 MINUTES)

| PLASMID | β-GALACTOSIDASE-POSITIVE CELLS |
|---|---|
| β-Galactosidase | 39.4 +/− 10.8 |
| β-Galactosidase/HSF1(−) | 24.9 +/− 8.9 |

Transfected cultures were subjected to a severe heat shock (48° C./10 minutes; about 75% cell survival) or left untreated, and β-galactosidase-positive cells were counted the following day. Untreated, singly and doubly transfected cultures contained similar number of β-galactosidase-expressing cells. In the heat-shocked cultures, the presence of HSF1(−) increased cell killing by about 60% (p<0.05). Thus, the increase in Hsp levels occurring as a consequence of a stressful event has a significant, immediate protective effect.

EXAMPLE 2

Assessment of Activation or Enhancement of Expression of Endogenous hsp Genes by HSF Mutants Previous experiments showed that the 529 residue-long human HSF1 polypeptide is expressed and accumulates in human HeLa-CAT cells (Baler, R. et al., *J. Cell Physiol.* 117: 1151–9 (1992)) and HeLa cells transfected with a construct containing a human HSF1 cDNA gene (Baler, R. et al., *Mol. Cell. Biol.* 13: 2486–96 (1993)) under the control of the cytomegalovirus promoter (Zuo, J. et al., *Mol. Cell. Biol.* 15: 4319–30 (1995)). HSF1 synthesized from transfected genes is predominantly trimeric, HSE DNA binding and nuclear-localized (Zuo et al., 1995). However, in the absence of stress, the factor is incapable of activating the human hsp70B promoter-driven chloramphenicol acetyltransferase (CAT) reporter genes present in HeLa-CAT cells. To test whether exogenously derived, trimeric HSF1 could be activated by heat shock, the HSE DNA-binding domain located at the extreme amino terminus of HSF1 was replaced with the DNA-binding domain of bacterial repressor LexA (substituting the first 78 residues of HSF1 with a 87 residues-long LexA segment using standard recombinant DNA procedures). Like HSF1 itself, the resulting LexA-HSF1 chimera was found to accumulate as a DNA-binding but transcriptionally inactive trimer in the absence of stress. Heat shock was capable of activating the chimeric factor, as shown by the ability of the factor to stimulate the expression of a reporter gene controlled by a promoter containing LexA binding sites. Deletions as well as certain substitutions in the region between residues 186 and 315 were found to enable HSF1 to activate the hsp70B reporter gene in HeLa-CAT cells in the absence of stress.

To determine whether such HSF1 deletion mutants could also activate or enhance the expression of endogenous hsp genes, HeLa-CAT cells, grown in Dulbecco's modified Eagle medium (DMEM) with 10% fetal bovine serum in a humidified 5% $CO_2$ atmosphere at 37° C., were co-transfected with constructs containing, in expressible form, an HSF1d202–316 (HSF(+), lacking residues 203 to 315; the deletion factor is referred to below generically as mutHSF) cDNA and a bacterial beta-galactosidase gene, or were singly transfected with the beta-galactosidase construct. The original human HSF1 cDNA gene had been obtained by screening a human cDNA library with oligonucleotide probes of known sequence using standard technology (Baler, R. et al., *Mol. Cell. Biol.* 13: 2486–96 (1993)). The cDNA was re-cloned into vector pGEM3Zf(+), in between HindIII and EcoRI restriction sites. To prepare the mutHSF cDNA gene, advantage was taken of the presence of BamHI and SmaI restriction sites at residues 202 and 316. An oligonucleotide linker of the correct length was added at the BamHI site to allow in frame fusion to the sequence at the SmaI site (Zuo, J. et al., *Mol. Cell. Biol.* 14: 7557–68 (1994)). To bring the mutHSF gene under the control of the cytomegalovirus promoter, the gene was excised from pGEM3Zf by HindIII and EcoRI and inserted between the same sites in the polylinker region of vector pcDNA1 (Invitrogen). DNAs were prepared by standard procedures. Transfections were achieved by lipofection, using Lipofectamine™ solution (Gibco/BRL) according to the suggested protocol of the manufacturer. One or two days after transfection, cells were incubated for two hours with 80 uCi/ml of 3H-leucine (New England Nuclear; specific activity 5.18 tBq/mmol) in DMEM lacking leucine. Cells were then washed with medium, collected and lysed in three packed cell-volumes of 20 mM Hepes, pH7.9, 0.42 M NaCl, 1.5 mM $MgCl_2$, 0.2 mM EDTA, 0.5 mM dithiothreitol, 0.5 mM phenylmethylsulfonyl fluoride and 25% glycerol. The lysate was cleared by centrifugation at 12,000×g for 5 min at 4° C., and the amount of 3H-leucine-labeled protein was determined on an aliquot of the cleared lysate (extract) by TCA precipitation. Aliquots normalized to contain similar amounts of radiolabeled protein were used to measure beta-galactosidase activities by the standard colorimetric assay (ONPG hydrolysis) or were applied to 10% SDS-polyacrylamide gels. After electrophoresis, gels were treated with 10% sodium salicylate and exposed to X-ray film at −70° C. for an appropriate period of time. Even though results of assays of beta-galactosidase activities indicated that the cells had been successfully transfected, the experiment failed to provide evidence for enhanced synthesis of proteins with subunit molecular weights characteristic of major hsps. Assuming that the typically low transfection efficiency of mammalian cells obscured the observation of enhanced hsp expression in a small fraction of cells that had been transfected successfully, selection of transfected cells prior to analysis was attempted. The commercial "pHook" system was employed in this experiment (Chesnut, J. D., et al., *J. Immunol. Methods,* 193:17–27 (1996)). The Hook construct encodes a membrane-associated antibody, permitting cells expressing the antibody to be enriched by binding to magnetic beads loaded with antigen. Cells were cotransfected as before with the cytomegalovirus promoter-linked mutHSF gene and the Hook construct or were transfected with the Hook construct alone, and one and two days after transfection were harvested, incubated with antigen-containing magnetic beads and bound cells separated from unbound cells by means of a magnet. Extracts were prepared from bound cells as before and were analyzed by western blot using antibodies specific for hsp90, hsc73, hsp72, hsp60 and hsp27 (StressGen Biotechnologies Corp.). No evidence for activation of endogenous hsp genes by mutHSF was obtained, presumably as a result of insufficient selectivity of the separation procedure.

To avoid the apparent problem with low transfection efficiency altogether, the transfection approach was substituted by an infection approach. The mutHSF cDNA (HSF1 (+)) was inserted behind a cytomegalovirus promoter flanked by adenoviral sequences in plasmid vector AC CMV pLpA SR (+). Human 293 cells expressing the adenovirus E1A region genes were co-transfected with plasmid vector lacking an inserted foreign gene or plasmid vector containing mutHSF and plasmid JM17 containing the bulk of adenovirus sequences. By recombination of sequences on the two types of plasmids, adenoviral genomes were created that lacked the EIA region (replication-defective) but contained a cytomegalovirus promoter (control virus) or a cytomegalovirus promoter linked to the mutHSF gene and that were packaged into defective virus particles (mutHSF virus)(See Graham and Prevec, 1991, for a description of the methodology used to create the adenovirus vehicles). Viral plaques were isolated and expanded, and the viral genomes were analyzed by restriction enzyme digestion. Infections with viruses were performed at a multiplicity of infection (MOI) of about 5. Three groups of 50% confluent cultures of HeLa-CAT cells were set up. The first group was infected with mutHSF virus (Ade-HSF1(+)), the second group with control virus (Ade), and the third group received no virus. The three groups of cultures were then incubated for 15, 24 and 36 hours, respectively, and were subsequently harvested. Extracts were prepared as before.

To assess mutHSF expression in infected cells, a western blot analysis of cell extracts was carried out using a specific antibody against human HSF1 (Baler, R. et al., *Mol. Cell. Biol.* 13: 2486–96 (1993)) that was detected chemiluminescently (Zuo, J. et al., *Mol. Cell. Biol.* 15: 4319–30 (1995)). Results showed barely detectable expression of mutHSF at 15 hours and copious amounts of mutHSF at 24 and 36 hours after infection. Only background levels were present in extracts from uninfected or control virus-infected cells.

To test whether mutHSF was transcriptionally active, rates of expression of the hsp70B-CAT reporter genes present in HeLa-CAT cells were estimated by CAT activity assays conducted as described by Gorman et al. (Gorman, C. M. et al., *Mol. Cell. Biol.* 2: 1044–51 (1982)). In this experiment, parallel cultures were infected with mutHSF and control virus. Control cultures were incubated at 37° C. for the duration of the experiment, or were subjected to a 43° C./30 min heat shock. After overnight incubation at 37° C., cells were harvested, and extracts prepared and analyzed for CAT activity. Results showed that mutHSF activated the hsp70B-CAT genes equally as well as or better than endogenous HSF1 activated by a moderately severe heat shock.

To determine whether mutHSF was capable of enhancing/activating the expression of endogenous hsps, extracts from uninfected cells or from cells infected with mutHSF or control virus and postincubated for 15, 24, and 36 hours (see above) were analyzed by anti-hsp western blot. mutHSF drastically increased expression of hsp72, the major inducible member of the hsp70 family, and of hsp27 (also known as hsp25). Even synthesis of the typically less inducible hsps such as hsp73 (also known as hsc70) and hsp60 was enhanced. Hsp90 levels were also clearly increased in mutHSF virus-infected cells. The hsp90 antibody used may have detected both the inducible and constitutive forms of hsp90, masking a more dramatic induction of the inducible form. Extracts from control virus-infected cells did not contain larger amounts of hsp than uninfected cells. The blots were also probed with an anti-actin antibody to confirm equal protein loading in different lanes. These observations strongly suggest that mutHSF alone is able to increase the intracellular levels of the major hsp.

To corroborate these findings as well as to examine whether expression of mutHSF enhances the expression of non-hsp, a similar experiment was conducted in which cells were exposed to 3H-leucine for two hours immediately prior to harvest in order to radiolabel newly synthesized proteins. Cell extracts were subjected to SDS-PAGE and fluorography (see above for procedures). mutHSF virus-infected cells, but not control virus-infected cells displayed enhanced synthesis of polypeptides with molecular weights of 90, 72, 60 and 25 kDa, corresponding in size to hsp90, hsp70 members, hsp60 and hsp25. Increased synthesis of proteins with subunit molecular weights not in the range of known hsps was not observed.

To generalize the above findings, newly synthesized polypeptides in infected mutHSF and control virus and uninfected human MRC5 cells, grown under the same conditions as HeLa cells, were analyzed as in the previous experiment. A similar pattern of induced protein expression to that of HeLa cells was detected in the MRC5 cells.

Hsp genes were previously shown to be activated by denatured proteins, and it has been proposed that accumulation of nonnative proteins may be an essential intermediate step in the activation of hsp genes (Ananthan, J. et al., *Science* 232: 522–4 (1986)). Therefore, it is possible that mutHSF is a nonnative protein capable of activating endogenous HSF1. However, this possibility can be virtually excluded in view of the following observations. First, effective activation of HSF1 and hsp genes by nonnative proteins requires large quantities of completely denatured proteins (Ananthan et al., 1986, and Applicant's observations), and only selected proteins are capable of triggering activation after denaturation. Second, based on the following criteria, mutHSF is a fully native protein: it is similarly active in HSE DNA-binding assays as (activated) wildtype HSF1 and is capable of trimerization and quantitative nuclear relocalization (Zuo, J. et al., *Mol. Cell. Biol.* 15: 4319–30 (1995)). Furthermore, as discussed above, replacement of the HSE DNA-binding domain in HSF1 with a LexA DNA-binding domain yields a chimeric factor (LexA-HSF1) capable of heat-regulated activation of a reporter gene under the control of a promoter containing LexA binding sites. In this experiment, HeLa cells were cotransfected with a LexA-CAT reporter gene construct and a construct containing the LexA-HSF1 gene in an expressible form. Heat treatment was applied one day after transfection, and cells were harvested and assayed for CAT activity two days after transfection. Heat-treated but not untreated LexA-HSF1-cotransfected cells had high levels of CAT activity. Cells transfected with only the reporter gene construct showed undetectable levels of CAT activity, whether they had been heat-treated or not. Introduction of the residue 203–315 deletion (present in mutHSF) into LexA-HSF1 resulted in a factor (LexA-mutHSF) capable of constitutively activating the LexA-CAT reporter gene. Thus, the deletion results in a gain of function. The experiment clearly showed that the chimeric factor harboring the deletion is a fully active transcription factor. In order to function as a transcription factor, LexA-mutHSF and, by extension, mutHSF, must have a virtually completely native conformation, since previous structure-function analysis of HSF1 showed that most deletions in the regions amino terminal of residue 203 and carboxyterminal of residue 277 result in either non-trimeric, non-DNA-binding, non-nuclear or transcriptionally inactive factor (Zuo et al., 1995). To address directly the possibility that the residue 203–315 deletion could render HSF1 a sufficiently nonnative protein to trigger hsp activation, the ability of LexA-mutHSF to activate the hsp70B-CAT reporter genes of HeLa-CAT cells was tested. In this experiment mutHSF expressed from transfected genes strongly activated the hsp70B-CAT genes but no detectable reporter activity was evident in cells expressing LexA-HSF1 or LexA-mutHSF. Anti-HSF1 western blot of the same extracts showed that LexA-HSF1 and LexA-mutHSF were substantially overexpressed when compared to endogenous HSF1 (especially when taking into account that only about 10% of cells were successfully transfected). In this particular experiment, LexA-mutHSF was expressed at a higher level than mutHSF. These observations demonstrate that mutHSF is a highly active transcription factor that activates endogenous hsp genes directly rather than by triggering the activation of endogenous HSF1.

Example 3

Assessment of Acquisition of Protected Phenotype in Cells in which hsp Expression is Induced by mutHSF To determine whether cells induced to express hsp by mutHSF acquire a protected phenotype, cells were assayed for their susceptibility to heat-induced killing, to detachment from the substratum as an indication of the integrity of cytoskeletal architecture and to heat-induced cell cycle arrest in G2/M phase.

To estimate the protective effect of mutHSF-induced hsp against heat-induced cell killing, groups of HeLa-CAT cultures were infected with mutHSF (Ade-HSF1(+)) or control virus (Ade), or were left uninfected. One day after infection, the cultures were exposed to a 49° C./20 min heat shock and then returned to 37° C. and incubated further for 15 hours. Survival of cells was estimated by scoring trypan blue-excluding cells using a haemocytometer.

TABLE 4

CELL SURVIVAL AFTER HEAT SHOCK
(49° C./20 MINUTES)

| Vector | Treatment | Cell Survival (%) |
| --- | --- | --- |
| None | None | 100 |
| None | Heat shock | 39 +/− 3 |

TABLE 4-continued

CELL SURVIVAL AFTER HEAT SHOCK
(49° C./20 MINUTES)

| Vector | Treatment | Cell Survival (%) |
| --- | --- | --- |
| Ade-HSF1(+) | Heat shock | 98 +/− 3 |
| Ade | Heat shock | 33 +/− 8 |

Results demonstrated that the heat shock regime killed over 60% of cells. Control virus-infected cells were killed at the same rate, but mutHSF virus-infected cells were essentially 100% protected. Thus, overexpression of the normal set of hsp mediated by mutHSF affords effective protection against heat-induced cell killing.

Even heat treatments that only result in marginal killing cause cells to detach transiently from the cell culture surface. This stress-induced detachment was followed as a measure of disruption of the normal cytoskeletal organization. Infected and uninfected cultures were subjected to a 47° C./20 min heat shock. Immediately following the heat treatment, cultures were washed to remove dislodged cells, and cells remaining on the dish were incubated further at 37° C. for 15 hours before counting.

TABLE 5

CELL ATTACHMENT TO SUBSTRATUM AFTER
HEAT SHOCK (47° C./20 MINUTES)

| Vector | Treatment | Cells Attached (%) |
| --- | --- | --- |
| None | None | 100 |
| None | Heat shock | 15 +/− 2 |
| Ade-HSF1(+) | Heat shock | 76 +/− 2 |

Heat treatment caused about 85% of cells to detach from the surface. mutHSF virus-infected cells, but not control virus-infected cells were largely protected, suggesting that overexpression of hsp mediated by mutHSF prevents stress-induced disruption of cytoskeletal architecture.

Experiments were also conducted to determine whether mutHSF-induced hsp synthesis can-prevent heat-induced G2/M cell cycle arrest. To test for recovery from translational arrest following heat shock, cells infected with Ade-HSF1(+) or Ade were subjected to a 44° C./30 minute heat shock and then allowed to recover at 37° C.

TABLE 6

RECOVERY OF TRANSLATION AFTER HEAT
SHOCK (44° C./30 MIN.)

| | Relative incorporation of $^3$H-Leucine | | |
| --- | --- | --- | --- |
| Vector | Before HS | During HS | Recovery 1 hour |
| None | 100 | 9 | 14 |
| Ade-HSF1(+) | 105 | 12 | 98 |
| Ade | 119 | 8 | 9 |

Figure 3A:
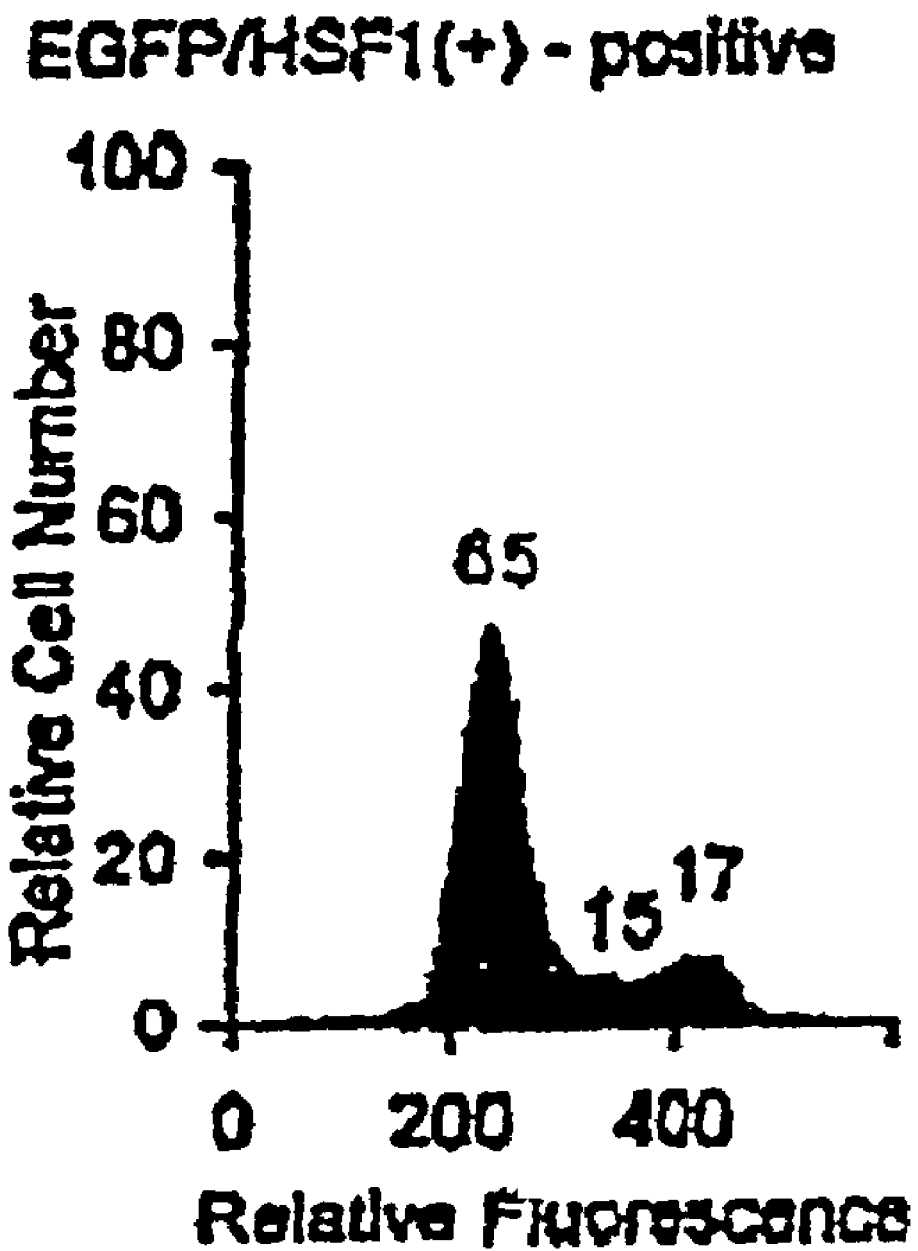
FIGS. 3A–3B are graphs of relative fluorescence versus relative cell number showing that numbers of HSF1(+)-expressing cells in S and G2/M phases were found to be somewhat elevated.
Figure 3B:
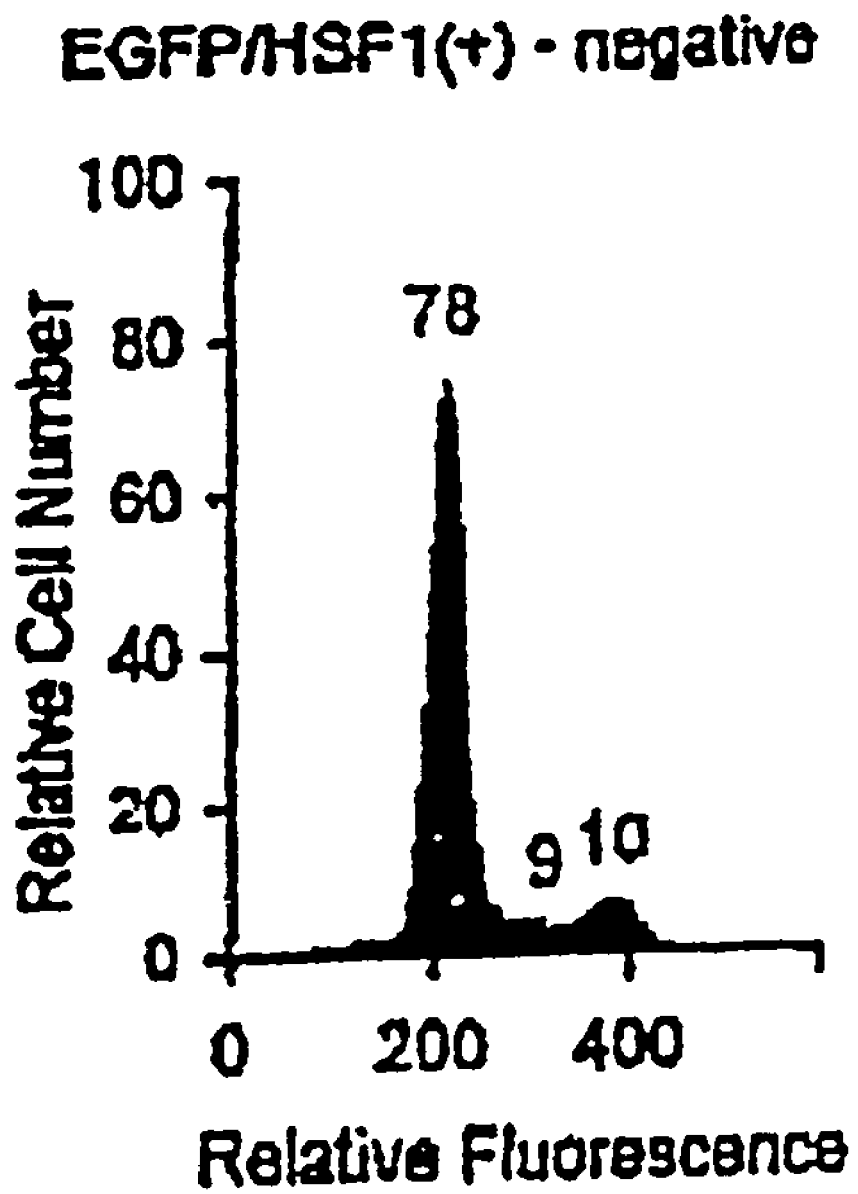

Protein synthesis dropped to about 10% of the normal rate during heat shock but, after a 1 hour recovery period, returned to pre-shock level in HSF1(+)-expressing but not control cells. Thus, increased accumulation of Hsps mediated by HSF1(+) effectively protected cells against severe heat stress. In the course of work with adenoviral vectors (both mutHSF and control virus), it was observed that the viruses reduced the growth rate of infected cells. To avoid ambiguities in the interpretation of results, it was decided to perform experiments dealing with cell cycle arrest with a transfection, rather than an infection, approach. To overcome the earlier difficulties in separating successfully transfected cells from untransfected cells, experiments with the green fluorescent protein (GFP) as a marker of transfection were initiated. Cells expressing GFP from a cytomegalovirus promoter-driven gene (EGFP-C1 DNA) could be separated satisfactorily from naive cells. Cultures were cotransfected with a mutHSF gene and EGFP-C1 DNA. Three days after transfection, cells were removed from culture dishes with 0.04% EDTA/phosphate-buffered saline (PBS) and suspended in PBS. Fluorescence-activated cell sorting and analyses of DNA content were performed on a FACStar Plus machine (Becton-Dickinson, San Jose, Calif.) configured as described elsewhere (Parks, D. R. et al., In: *The Handbook of Experimental Immunology*, 4th Edition. Vol. 29. pp. 1–29, 1986). Excitation wave length was 488 nm, and detection lengths were 650 nm (long pass) for propidium iodide and 520 nm (narrow band) for fluorescence by GFP. Extracts from sorted cells were analyzed by western blot. mutHSF was detected in cells sorted as positive for GFP, but not in cells sorted as negative compare. See Table 2. GFP-positive cells had increased levels of hsp72 and hsp90 compared to GFP-negative cells. The level of hsp72 induction was substantial: GFP-positive cells had similar hsp72 levels as untransfected cells heat-shocked one day prior to harvest and analysis. To examine effects on cell cycle arrest, HeLa-CAT cultures were cotransfected with the mutHSF gene and EGFP-C1 DNA or were mock transfected (transfected with EGFP construct alone), heat-treated one day later and harvested for FACS after an additional day of incubation at 37° C. In one type of experiment, HSF1(+)-expressing and not-expressing cells were isolated by FACS and replated (on day one), and their proliferation was followed between days two and four (FIG. 2). Results indicated that elevated Hsp levels severely inhibited cell proliferation. Similar results were obtained from another type of experiment, in which cells were not sorted, and numbers of transfected cells were determined from total cell numbers and cytometric assessments of the fraction of cells expressing EGFP. The latter experiment also revealed that cells proliferated between days one and two, i.e., that proliferation only stopped on day two. After fractionation by FACS based on GFP fluorescence, cells in GFP-positive and negative pools were fixed with 70% ethanol for 18 hours, stained with 50 ug/ml propidium iodide (Molecular Probes) and then reanalyzed by flow cytometry to determine DNA content. This analysis revealed that the GFP-positive pool representing mutHSF-containing and hsp-overexpressing cells contained a much lower proportion of cells in G2/M phase than the GFP-negative pool. Expression of mutHSF was verified by western blot. When, in the experiment shown in FIG. 2, cells from the last time point (day 4) were analyzed for DNA content, numbers of HSF1(+)-expressing cells in S and G2/M phases were found to be somewhat elevated (FIGS. 3A–3B). Cytometric analysis showed that the average cell size did not change appreciably. Thus, increased Hsp levels precipitously slow the rate of progression through the cell cycle, without arresting cells in a particular position in the cycle. Inhibition of progression appears to be somewhat less severe between G1 and S, with the result that, with time, there is some accumulation of cells in S and G2/M phases. DNA replication was assessed (on day 2) by $^3$H-thymidine incorporation and was found to be reduced 4–5 fold in HSF1(+)-expressing cells compared to control cells.

TABLE 9

RATES OF PROTEIN AND DNA SYNTHESIS IN HSF1(+)-EXPRESSING CELLS

| Constructs | Relative incorporation of | |
|---|---|---|
| | $^3$H-leucine (%) | $^3$H-thymidine (%) |
| None | 100 | 100 |
| EGFP/HSF1(+), sorted as EGFP-negative | 93 | 100 |
| EGFP/HSF1(+), sorted as EGFP-positive | 93 | 23 |

Protein synthesis was examined by pulse-labeling cells with $^3$H-leucine followed by TCA precipitation of labeled proteins (Table 9; data from day 4 are shown) or analysis by SDS-PAGE and fluorography. Elevated Hsp levels were found to neither affect the rate of protein synthesis nor grossly alter relative amounts of non-Hsp proteins synthesized. To obtain an estimate of the transcriptional (RNA polymerase II) capability of cells with elevated Hsp levels, cells were infected with Ade-HSF1(+) or Ade and, one day later, were transfected with the EGFP construct.

TABLE 10

RNA POLYMERASE II TRANSCRIPTION IN HSF1(+)-EXPRESSING CELLS

| Vector/Construct | Transfection Efficiency (%) | Mean Relative Fluorescence |
|---|---|---|
| None/EGFP | 39 +/− 5 | 1403 +/− 145 |
| Ade/EGFP | 46 +/− 1 | 1525 +/− 1 |
| Ade-HSF1(+)/EGFP | 42 +/− 0 | 848 +/− 27 |

Cytometric quantitation indicated that cells with elevated Hsp levels were capable of substantial EFGP expression, although absolute levels were somewhat reduced (by about 45%) compared with control cells. In summary, the idealized tolerant state caused by elevated Hsp levels is characterized by severely inhibited cell cycle progression and DNA replication, but normal translation and substantial transcription activity. This nonproliferative, metabolic state can be maintained for several days. Thus, overexpression of hsp mediated by mutHSF protects cells against heat-induced cell cycle arrest. This protective effect-was not seen in cells singly transfected with EGFP-C1 DNA and examined as described above.

HSF1(+)-expressing cells were also partially protected against medically relevant stresses such as toxicity from cyclophosphamide, a chemotherapy drug with known hepatotoxicity, and simulated ischemia. Exposure (24 hour) of human hepatocyte-derived HspG2 cells to cyclophosphamide (20 mM) caused substantial mortality (38%) that was reduced by 55% by the presence of HSF1.

TABLE 7

MORTALITY FROM EXPOSURE TO CYCLOPHOSPHAMIDE

| Vector | Cyclophos. | Relative LDH Release | Mortality |
|---|---|---|---|
| Ade | None | 21 | 13 |
| Ade | 20 mM | 100 +/− 24 | 51 +/− 1 |
| Ade-HSF1(+) | None | 25 | 13 |
| Ade-HSF1(+) | 20 mM | 70 +/− 18 | 30 +/− 1 |

When mortality was assessed by the lactate dehydrogenase (LDH) leakage assay, expression of HSF1(+) resulted in a 43% reduction that compared well with the 25% reduction reported for heat preconditioning (Salminen, W. F. et al., *Toxicol. Appl. Pharmacol.*, 141:117–123 (1996)). HSF1(+) also decreased the mortality of HepG2 cells subjected to simulated ischemia by more than 50% (Heat preconditioning had a 40% effect).

TABLE 8

MORTALITY FROM SIMULATED ISCHEMIA

| Vector | Pretreatment | Relative LDH Release |
|---|---|---|
| None | None | 100 +/− 11 |
| None | Heat shock | 60 +/− 0 |
| Ade-HSF1(+) | None | 47 +/− 2 |
| Ade | None | 94 =/− 8 |

Thus, an increase in Hsp levels mediated by HSF1(+), i.e., by deregulation of HSF1 activity, is generally cytoprotective.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method for enhancing the immunogenicity of a tumor cell in an individual, comprising introducing into the tumor cell of the individual a positively-acting mutHSF in a quantity sufficient for the positively-acting mutHSF to enhance hsp synthesis in the tumor cell, thereby targeting the tumor cell for immune recognition and elimination.

2. The method of claim 1, whereby the positively acting mutHSF is administered to the individual in a quantity sufficient and under conditions appropriate for the positively acting mutHSF to be introduced into the tumor cell of the individual.

3. The method of claim 1, wherein the positively acting mutHSF is introduced into the tumor cell ex vivo.

4. The method of claim 1, wherein the positively-acting mutHSF comprises a heat shock element DNA-binding domain, a heat shock transcription factor oligomerization domain, a nuclear localization signal and a transcription activation domain.

5. The method of claim 1, wherein the positively-acting mutHSF is derived from a heat shock transcription factor by mutation in a region corresponding to about residue 180 to about residue 315 in human HSF1.

6. The method of claim 1, wherein the positively-acting mutHSF is provided in the form of a vector comprising a nucleic acid sequence encoding the positively-acting mutHSF, and the positively-acting mutHSF is expressed from the nucleic acid sequence.

7. The method according to claim 6, wherein the vector is selected from the group consisting of a plasmid, an animal viral vector, a DNA capable of replicating in the tumor cell and a DNA capable of being maintained in the tumor cell.

* * * * *

SEQUENCE LISTING

<160> NUMBER OF SEQ ID NOS: 3

<210> SEQ ID NO 1
<211> LENGTH: 2156
<212> TYPE: DNA
<213> ORGANISM: Artificial Sequence
<220> FEATURE:

<223> OTHER INFORMATION: Unknown
<220> FEATURE:
<221> NAME/KEY: CDS
<222> LOCATION: (161)...(1747)

<400> SEQUENCE: 1

| | | |
|---|---|---|
| cgggcccgtt gcaagatggc ggcggccatg ctgggccccg ggctgtgtg tgcgcagcgg | | 60 |
| gcggcggcgc ggcccggaag gctggcgcgg cgacggcgtt agcccggccc tcggcccctc | | 120 |
| tttgcggccg ctccctccgc ctattccctc cttgctcgag atg gat ctg ccc gtg<br>                                                       Met Asp Leu Pro Val<br>                                                          1             5 | | 175 |
| ggc ccc ggc gcg gcg ggg ccc agc aac gtc ccg gcc ttc ctg acc aag<br>Gly Pro Gly Ala Ala Gly Pro Ser Asn Val Pro Ala Phe Leu Thr Lys<br>                  10                          15                        20 | | 223 |
| ctg tgg acc ctc gtg agc gac ccg gac acc gac gcg ctc atc tgc tgg<br>Leu Trp Thr Leu Val Ser Asp Pro Asp Thr Asp Ala Leu Ile Cys Trp<br>                  25                          30                        35 | | 271 |
| agc ccg agc ggg aac agc ttc cac gtg ttc gac cag ggc cag ttt gcc<br>Ser Pro Ser Gly Asn Ser Phe His Val Phe Asp Gln Gly Gln Phe Ala<br>                  40                          45                        50 | | 319 |
| aag gag gtg ctg ccc aag tac ttc aag cac aac aac atg gcc agc ttc<br>Lys Glu Val Leu Pro Lys Tyr Phe Lys His Asn Asn Met Ala Ser Phe<br> 55                        60                          65 | | 367 |
| gtg cgg cag ctc aac atg tat ggc ttc cgg aaa gtg gtc cac atc gag<br>Val Arg Gln Leu Asn Met Tyr Gly Phe Arg Lys Val Val His Ile Glu<br> 70                        75                        80                        85 | | 415 |
| cag ggc ggc ctg gtc aag cca gag aga gac gac acg gag ttc cag cac<br>Gln Gly Gly Leu Val Lys Pro Glu Arg Asp Asp Thr Glu Phe Gln His<br>                        90                          95                        100 | | 463 |
| cca tgc ttc ctg cgt ggc cag gag cag ctc ctt gag aac atc aag agg<br>Pro Cys Phe Leu Arg Gly Gln Glu Gln Leu Leu Glu Asn Ile Lys Arg<br>                  105                       110                       115 | | 511 |
| aaa gtg acc agt gtg tcc acc ctg aag agt gaa gac ata aag atc cgc<br>Lys Val Thr Ser Val Ser Thr Leu Lys Ser Glu Asp Ile Lys Ile Arg<br>                  120                       125                       130 | | 559 |
| cag gac agc gtc acc aag ctg ctg acg gac gtg cag ctg atg aag ggg<br>Gln Asp Ser Val Thr Lys Leu Leu Thr Asp Val Gln Leu Met Lys Gly<br>135                        140                        145 | | 607 |
| aag cag gag tgc atg gac tcc aag ctc ctg gcc atg aag cat gag aat<br>Lys Gln Glu Cys Met Asp Ser Lys Leu Leu Ala Met Lys His Glu Asn<br>150                        155                        160                        165 | | 655 |
| gag gct ctg tgg cgg gag gtg gcc agc ctt cgg cag aag cat gcc cag<br>Glu Ala Leu Trp Arg Glu Val Ala Ser Leu Arg Gln Lys His Ala Gln<br>                  170                       175                       180 | | 703 |
| caa cag aaa gtc gtc aac aag ctc att cag ttc ctg atc tca ctg gtg<br>Gln Gln Lys Val Val Asn Lys Leu Ile Gln Phe Leu Ile Ser Leu Val<br>                  185                       190                       195 | | 751 |
| cag tca aac cgg atc ctg ggg gtg aag aga aag atc ccc ctg atg ctg<br>Gln Ser Asn Arg Ile Leu Gly Val Lys Arg Lys Ile Pro Leu Met Leu<br>                  200                       205                       210 | | 799 |
| aac gac agt ggc tca gca cat tcc atg ccc aag tat agc cgg cag ttc<br>Asn Asp Ser Gly Ser Ala His Ser Met Pro Lys Tyr Ser Arg Gln Phe<br>                  215                       220                       225 | | 847 |
| tcc ctg gag cac gtc cac ggc tcg ggc ccc tac tcg gcc ccc tcc cca<br>Ser Leu Glu His Val His Gly Ser Gly Pro Tyr Ser Ala Pro Ser Pro<br>230                        235                        240                        245 | | 895 |
| gcc tac agc agc tcc agc ctc tac gcc cct gat gct gtg gcc agc tct<br>Ala Tyr Ser Ser Ser Ser Leu Tyr Ala Pro Asp Ala Val Ala Ser Ser<br>                  250                       255                       260 | | 943 |

```
                                                     -continued gga ccc atc atc tcc gac atc acc gag ctg gct cct gcc agc ccc atg      991
Gly Pro Ile Ile Ser Asp Ile Thr Glu Leu Ala Pro Ala Ser Pro Met
            265                 270                 275 gcc tcc ccc ggc ggg agc ata gac gag agg ccc cta tcc agc agc ccc     1039
Ala Ser Pro Gly Gly Ser Ile Asp Glu Arg Pro Leu Ser Ser Ser Pro
        280                 285                 290 ctg gtg cgt gtc aag gag gag ccc ccc agc ccg cct cag agc ccc cgg     1087
Leu Val Arg Val Lys Glu Glu Pro Pro Ser Pro Pro Gln Ser Pro Arg
    295                 300                 305 gta gag gag gcg agt ccc ggg cgc cca tct tcc gtg gac acc ctc ttg     1135
Val Glu Glu Ala Ser Pro Gly Arg Pro Ser Ser Val Asp Thr Leu Leu
310                 315                 320                 325 tcc ccg acc gcc ctc att gac tcc atc ctg cgg gag agt gaa cct gcc     1183
Ser Pro Thr Ala Leu Ile Asp Ser Ile Leu Arg Glu Ser Glu Pro Ala
                330                 335                 340 ccc gcc tcc gtc aca gcc ctc acg gac gcc agg ggc cac acg gac acc     1231
Pro Ala Ser Val Thr Ala Leu Thr Asp Ala Arg Gly His Thr Asp Thr
            345                 350                 355 gag ggc cgg cct ccc tcc ccc ccg ccc acc tcc acc cct gaa aag tgc     1279
Glu Gly Arg Pro Pro Ser Pro Pro Pro Thr Ser Thr Pro Glu Lys Cys
        360                 365                 370 ctc agc gta gcc tgc ctg gac aag aat gag ctc agt gac cac ttg gat     1327
Leu Ser Val Ala Cys Leu Asp Lys Asn Glu Leu Ser Asp His Leu Asp
    375                 380                 385 gct atg gac tcc aac ctg gat aac ctg cag acc atg ctg agc agc cac     1375
Ala Met Asp Ser Asn Leu Asp Asn Leu Gln Thr Met Leu Ser Ser His
390                 395                 400                 405 ggc ttc agc gtg gac acc agt gcc ctg ctg gac ctg ttc agc ccc tcg     1423
Gly Phe Ser Val Asp Thr Ser Ala Leu Leu Asp Leu Phe Ser Pro Ser
                410                 415                 420 gtg acc gtg ccc gac atg agc ctg cct gac ctt gac agc agc ctg gcc     1471
Val Thr Val Pro Asp Met Ser Leu Pro Asp Leu Asp Ser Ser Leu Ala
            425                 430                 435 agt atc caa gag ctc ctg tct ccc cag gag ccc ccc agg cct ccc gag     1519
Ser Ile Gln Glu Leu Leu Ser Pro Gln Glu Pro Pro Arg Pro Pro Glu
        440                 445                 450 gca gag aac agc agc ccg gat tca ggg aag cag ctg gtg cac tac aca     1567
Ala Glu Asn Ser Ser Pro Asp Ser Gly Lys Gln Leu Val His Tyr Thr
    455                 460                 465 gcg cag ccg ctg ttc ctg ctg gac ccc ggc tcc gtg gac acc ggg agc     1615
Ala Gln Pro Leu Phe Leu Leu Asp Pro Gly Ser Val Asp Thr Gly Ser
470                 475                 480                 485 aac gac ctg ccg gtg ctg ttt gag ctg gga gag ggc tcc tac ttc tcc     1663
Asn Asp Leu Pro Val Leu Phe Glu Leu Gly Glu Gly Ser Tyr Phe Ser
                490                 495                 500 gaa ggg gac ggc ttc gcc gag gac ccc acc atc tcc ctg ctg aca ggc     1711
Glu Gly Asp Gly Phe Ala Glu Asp Pro Thr Ile Ser Leu Leu Thr Gly
            505                 510                 515 tcg gag cct ccc aaa gcc aag gac ccc act gtc tcc tagaggcccc         1757
Ser Glu Pro Pro Lys Ala Lys Asp Pro Thr Val Ser
        520                 525 ggaggagctg ggccagccgc ccaccccac ccccagtgca gggctggtct tggggaggca    1817 ggcagcctc gcgtcttgg gcactggtgg gtcggccgcc atagcccag taggacaaac      1877 gggctcgggt ctgggcagca cctctggtca ggagggtcac cctggcctgc cagtctgcct   1937
tcccccaacc ccgtgtcctg tggtttggtt ggggcttcac agccacacct ggactgaccc   1997
tgcaggttgt tcatagtcag aattgtattt tggattttta cacaactgtc ccgttccccg   2057
ctccacagag atacacagat atatacacac agtggatgga cggacaagac aggcagagat   2117
```

```
ctataaacag acaggctcta aaaaaaaaaa aaaaaaaa                                  2156
```

<210> SEQ ID NO 2
<211> LENGTH: 529
<212> TYPE: PRT
<213> ORGANISM: Artificial Sequence
<220> FEATURE:
<223> OTHER INFORMATION: Unknown

<400> SEQUENCE: 2

```
Met Asp Leu Pro Val Gly Pro Gly Ala Ala Gly Pro Ser Asn Val Pro
 1               5                  10                  15

Ala Phe Leu Thr Lys Leu Trp Thr Leu Val Ser Asp Pro Asp Thr Asp
            20                  25                  30

Ala Leu Ile Cys Trp Ser Pro Ser Gly Asn Ser Phe His Val Phe Asp
        35                  40                  45

Gln Gly Gln Phe Ala Lys Glu Val Leu Pro Lys Tyr Phe Lys His Asn
    50                  55                  60

Asn Met Ala Ser Phe Val Arg Gln Leu Asn Met Tyr Gly Phe Arg Lys
 65                  70                  75                  80

Val Val His Ile Glu Gln Gly Gly Leu Val Lys Pro Glu Arg Asp Asp
                85                  90                  95

Thr Glu Phe Gln His Pro Cys Phe Leu Arg Gly Gln Glu Gln Leu Leu
            100                 105                 110

Glu Asn Ile Lys Arg Lys Val Thr Ser Val Ser Thr Leu Lys Ser Glu
        115                 120                 125

Asp Ile Lys Ile Arg Gln Asp Ser Val Thr Lys Leu Leu Thr Asp Val
    130                 135                 140

Gln Leu Met Lys Gly Lys Gln Glu Cys Met Asp Ser Lys Leu Leu Ala
145                 150                 155                 160

Met Lys His Glu Asn Glu Ala Leu Trp Arg Glu Val Ala Ser Leu Arg
                165                 170                 175

Gln Lys His Ala Gln Gln Gln Lys Val Val Asn Lys Leu Ile Gln Phe
            180                 185                 190

Leu Ile Ser Leu Val Gln Ser Asn Arg Ile Leu Gly Val Lys Arg Lys
        195                 200                 205

Ile Pro Leu Met Leu Asn Asp Ser Gly Ser Ala His Ser Met Pro Lys
    210                 215                 220

Tyr Ser Arg Gln Phe Ser Leu Glu His Val His Gly Ser Gly Pro Tyr
225                 230                 235                 240

Ser Ala Pro Ser Pro Ala Tyr Ser Ser Ser Leu Tyr Ala Pro Asp
                245                 250                 255

Ala Val Ala Ser Ser Gly Pro Ile Ile Ser Asp Ile Thr Glu Leu Ala
            260                 265                 270

Pro Ala Ser Pro Met Ala Ser Pro Gly Gly Ser Ile Asp Glu Arg Pro
        275                 280                 285

Leu Ser Ser Ser Pro Leu Val Arg Val Lys Glu Glu Pro Pro Ser Pro
    290                 295                 300

Pro Gln Ser Pro Arg Val Glu Glu Ala Ser Pro Gly Arg Pro Ser Ser
305                 310                 315                 320

Val Asp Thr Leu Leu Ser Pro Thr Ala Leu Ile Asp Ser Ile Leu Arg
                325                 330                 335

Glu Ser Glu Pro Ala Pro Ala Ser Val Thr Ala Leu Thr Asp Ala Arg
            340                 345                 350
```

```
Gly His Thr Asp Thr Glu Gly Arg Pro Pro Ser Pro Pro Pro Thr Ser
        355                 360                 365

Thr Pro Glu Lys Cys Leu Ser Val Ala Cys Leu Asp Lys Asn Glu Leu
    370                 375                 380

Ser Asp His Leu Asp Ala Met Asp Ser Asn Leu Asp Asn Leu Gln Thr
385                 390                 395                 400

Met Leu Ser Ser His Gly Phe Ser Val Asp Thr Ser Ala Leu Leu Asp
                405                 410                 415

Leu Phe Ser Pro Ser Val Thr Val Pro Asp Met Ser Leu Pro Asp Leu
            420                 425                 430

Asp Ser Ser Leu Ala Ser Ile Gln Glu Leu Leu Ser Pro Gln Glu Pro
        435                 440                 445

Pro Arg Pro Pro Glu Ala Glu Asn Ser Ser Pro Asp Ser Gly Lys Gln
    450                 455                 460

Leu Val His Tyr Thr Ala Gln Pro Leu Phe Leu Leu Asp Pro Gly Ser
465                 470                 475                 480

Val Asp Thr Gly Ser Asn Asp Leu Pro Val Leu Phe Glu Leu Gly Glu
                485                 490                 495

Gly Ser Tyr Phe Ser Glu Gly Asp Gly Phe Ala Glu Asp Pro Thr Ile
            500                 505                 510

Ser Leu Leu Thr Gly Ser Glu Pro Pro Lys Ala Lys Asp Pro Thr Val
        515                 520                 525

Ser
```

```
<210> SEQ ID NO 3
<211> LENGTH: 15
<212> TYPE: DNA
<213> ORGANISM: Artificial Sequence
<220> FEATURE:
<223> OTHER INFORMATION: Other Nucleic Acid
<220> FEATURE:
<221> NAME/KEY: misc_feature
<222> LOCATION: (1)...(15)
<223> OTHER INFORMATION: n = A,T,C or G

<400> SEQUENCE: 3
ngaannttcn ngaan                                                    15
```